United States Patent
Mitchell et al.

(10) Patent No.: US 9,370,557 B2
(45) Date of Patent: Jun. 21, 2016

(54) ADJUVANT COMPOUNDS

(75) Inventors: Timothy John Mitchell, Glasgow (GB); Lea-Ann Kirkham, Perth (AU); Graeme James Cowan, Glasgow (GB); Gillian Douce, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 1255 days.

(21) Appl. No.: 12/304,878

(22) PCT Filed: Jun. 15, 2007

(86) PCT No.: PCT/GB2007/002242
§ 371 (c)(1),
(2), (4) Date: Oct. 30, 2009

(87) PCT Pub. No.: WO2007/144647
PCT Pub. Date: Dec. 21, 2007

(65) Prior Publication Data
US 2010/0166795 A1    Jul. 1, 2010

Related U.S. Application Data

(60) Provisional application No. 60/813,826, filed on Jun. 15, 2006.

(51) Int. Cl.
*A61K 39/00* (2006.01)
*A61K 39/02* (2006.01)
*A61K 39/12* (2006.01)
*A61K 39/38* (2006.01)
(Continued)

(52) U.S. Cl.
CPC ............ *A61K 39/00* (2013.01); *A61K 39/0001* (2013.01); *A61K 39/092* (2013.01); *A61K 2039/53* (2013.01); *A61K 2039/57* (2013.01); *A61K 2039/6068* (2013.01)

(58) Field of Classification Search
CPC ..... A61K 39/00; A61K 39/02; A61K 39/013; A61K 39/0208; A61K 39/025; A61K 39/07; A61K 39/08
See application file for complete search history.

(56) References Cited

U.S. PATENT DOCUMENTS

| | | | | |
|---|---|---|---|---|
| 5,565,204 | A | * 10/1996 | Kuo et al. | 424/244.1 |
| 6,764,686 | B2 | * 7/2004 | Minetti et al. | 424/236.1 |
| 2002/0025323 | A1 | * 2/2002 | Paterson et al. | 424/192.1 |

(Continued)

FOREIGN PATENT DOCUMENTS

| | | | | |
|---|---|---|---|---|
| WO | WO 2005/042028 | * 5/2005 | | A61K 47/48 |
| WO | 2005/108419 | 11/2005 | | |
| WO | WO 2005/108580 | * 11/2005 | | C12N 15/31 |

OTHER PUBLICATIONS

Manuri et al., (Vaccine. Apr. 30, 2007. vol. 25(17):3302-10).*
Peters et al., (J. of Immunology. vol. 170(10):5176-5187).*
Ye et al., (Virus Research. 2003. vol. 97:7-16).*
Arai et al., (Protein Eng. 2001. 14(8): 529-532).*

(Continued)

*Primary Examiner* — J. Hines
(74) *Attorney, Agent, or Firm* — Kathleen D. Rigaut; Dann, Dorfman, Herrell and Skillman, P.C.

(57) ABSTRACT

The invention relates to the use of bacterial cytolysin proteins, such as pneumolysin, as adjuvants for stimulating or enhancing immune responses against co-administered target antigens. Desirably, the target antigen is provided as a fusion protein with the cytolysin. The inventors have found that cytolysins may be particularly effective for stimulation of mucosal immune responses against the target antigen.

13 Claims, 13 Drawing Sheets

(51) Int. Cl.
*A61K 45/00* (2006.01)
*A61K 39/09* (2006.01)

(56) References Cited

U.S. PATENT DOCUMENTS

2002/0131974 A1* 9/2002 Segal ............ 424/184.1
2003/0202985 A1 10/2003 Paterson
2005/0266512 A1* 12/2005 Buckley .......... C12Q 1/37
  435/23

OTHER PUBLICATIONS

Ling, Y., et al. "Enhanced immunogenicity of SIV Gag DNA vaccines encoding chimeric proteins containing a C-terminal segment of Listeriolysin O." Virus Research, 97(1): 7-16 (Nov. 2003).
Singh, R., et al. "Fusion to Listeriolysin O and Delivery by Listeria monocytogenes Enhances the Immunogenicity of HER-2/neu and Reveals Subdominant Epitopes in the FVB/N Mouse." Journal of Immunology, 175(6): 3663-3673 (Sep. 2005).
Lee, C.J., et al. "Mucosal immunity induced by pneumococcal glycoconjugate." Crit Rev Microbiol. 2005;31(3):137-44.

* cited by examiner

FIG. 8A

Pneumolysin from Streptococcus pneumoniae
Length: 471 AA          g.i. 47403 (X52474)

```
  1 MANKAVNDFI LAMNYDKKKL LTHQGESIEN RFIKEGNQLP DEFVVIERKK
 51 RSLSTNTSDI SVTATNDSRL YPGALLVVDE TLLENNPTLL AVDRAPMTYS
101 IDLPGLASSD SFLQVEDPSN SSVRGAVNDL LAKWHQDYGQ VNNVPARMQY
151 EKITAHSMEQ LKVKFGSDFE KTGNSLDIDF NSVHSGEKQI QIVNFKQIYY
201 TVSVDAVKNP GDVFQDTVTV EDLKQRGISA ERPLVYISSV AYGRQVYLKL
251 ETTSKSDEVE AAFEALIKGV KVAPQTEWKQ ILDNTEVKAV ILGGDPSSGA
301 RVVTGKVDMV EDLIQEGSRF TADHPGLPIS YTTSFLRDNV VATFQNSTDY
351 VETKVTAYRN GDLLLDHSGA YVAQYYITWN ELSYDHQGKE VLTPKAWDRN
401 GQDLTAHFTT SIPLKGNVRN LSVKIRECTG LAWEWWRTVY EKTDLPLVRK
451 RTISIWGTTL YPQVEDKVEN D
```

FIG. 8B

Perfringolysin O from Clostridium perfringens
Length: 500 AA          g.i. 144884 (AAA23270)

```
  1 MIRFKKTKLI ASIAMALCLF SQPVISFSKD ITDKNQSIDS GISSLSYNRN
 51 EVLASNGDKI ESFVPKEGKK TGNKFIVVER QKRSLTTSPV DISIIDSVND
101 RTYPGALQLA DKAFVENRPT ILMVKRKPIN INIDLPGLKG ENSIKVDDPT
151 YGKVSGAIDE LVSKWNEKYS STHTLPARTQ YSESMVYSKS QISSALNVNA
201 KVLENSLGVD FNAVANNEKK VMILAYKQIF YTVSADLPKN PSDLFDDSVT
251 FNDLKQKGVS NEAPPLMVSN VAYGRTIYVK LETTSSSKDV QAAFKALIKN
301 TDIKNSQQYK DIYENSSFTA VVLGGDAQEH NKVVTKDFDE IRKVIKDNAT
351 FSTKNPAYPI SYTSVFLKDN SVAAVHNKTD YIETTSTEYS KGKINLDHSG
401 AYVAQFEVAW DEVSYDKEGN EVLTHKTWDG NYQDKTAHYS TVIPLEANAR
451 NIRIKARECT GLAWEWWRDV ISEYDVPLTN NINVSIWGTT LYPGSSITYN
```

FIG. 8C

Intermedilysin from Streptococcus intermedius
Length: 532 AA          gi: 6729344 (NCBI - BAA89790)

```
  1  MKTKQNIARK LSRVVLLSTL VLSSAAPISA AFAETPTKPK AAQTEKKTEK
 51  KPENSNSEAA KKALNDYIWG LQYDKLNILT HQGEKLKNHS SREAFHRPGE
101  YVVIEKKKQS ISNATSKLSV SSANDDRIFP GALLKADQSL LENLPTLIPV
151  NRGKTTISVN LPGLKNGESN LTVENPSNST VRTAVNNLVE KWIQNYSKTH
201  AVPARMQYES ISAQSMSQLQ AKFGADFSKV GAPLNVDFSS VHKGEKQVFI
251  ANFRQVYYTA SVDSPNSPSA LFGSGITPTD LINRGVNSKT PPVYVSNVSY
301  GRAMYVKFET TSKSTKVQAA IDAVVKGAKL KAGTEYENIL KNTKITAVVL
351  GGNPGEASKV ITGNIDTLKD LIQKGSNFSA QSPAVPISYT TSFVKDNSIA
401  TIQNNTDYIE TKVTSYKDGA LTLNHDGAFV ARFYVYWEEL GHDADGYETI
451  RSRSWSGNGY NRGAHYSTTL RFKGNVRNIR VKVLGATGLA WEPWRLIYSK
501  NDLPLVPQRN ISTWGTTLHP QFEDKVVKDN TD
```

FIG. 8D

Alveolysin from Bacillus alvei
Length: 501 AA          gi: 142473 (NCBI - AAA22224)

```
  1  MKKKSNHLKG RKVLVSLLVS LQVFAFASIS SAAPTEPNDI DMGIAGLNYN
 51  RNEVLAIQGD QISSFVPKEG IQSNGKFIVV ERDKKSLTTS PVDISIVDSI
101  TNRTYPGAIQ LANKDFADNQ PSLVMAARKP LDISIDLPGL KNENTISVQN
151  PNYGTVSSAI DQLVSTWGEK YSSTHTLPAR LQYAESMVYS QNQISSALNV
201  NAKVLNGTLG IDFNAVANGE KKVMVAAYKQ IFYTVSAGLP NNPSDLFDDS
251  VTFAELARKG VSNEAPPLMV SNVAYGRTIY VKLETTSKSN DVQTAFKLLL
301  NNPSIQASGQ YKDIYENSSF TAVVLGGDAQ THNQVVTKDF NVIQSVIKDN
351  AQFSSKNPAY PISYTSVFLK DNSIAAVHNN TEYIETKTTE YSKGKIKLDH
401  SGAYVAQFEV YWDEFSYDAD GQEIVTRKSW DGNWRDRSAH FSTEIPLPPN
451  AKNIRIFARE CTGLAWEWWR TVVDEYNVPL ASDINVSIWG TTLYPKSSIT
501  H
```

FIG. 8E
Anthrolysin from Bacillus anthracis
Length: 512 AA          gi: 21397375 (NCBI - NC003995)

```
  1   MIFLNIKKNT  KRRKFLACLL  VSLCTIHYSS  ISFAETQAGN  ATGAIKNASD
 51   INTGIANLKY  DSRDILAVNG  DKVESFIPKE  SINSNGKFVV  VEREKKSLTT
101   SPVDILIIDS  VVNRTYPGAV  QLANKAFADN  QPSLLVAKRK  PLNISIDLPG
151   MRKENTITVQ  NPTYGNVAGA  VDDLVSTWNE  KYSTTHTLPA  RMQYTESMVY
201   SKSQIASALN  VNAKYLDNSL  NIDFNAVANG  EKKVMVAAYK  QIFYTVSAEL
251   PNNPSDLFDN  SVTFDELTRK  GVSNSAPPVM  VSNVAYGRTV  YVKLETTSKS
301   KDVQAAFKAL  LKNNSVETSG  QYKDIFEEST  FTAVVLGGDA  KEHNKVVTKD
351   FNEIRNIIKD  NAELSFKNPA  YPISYTSTFL  KDNATAAVHN  NTDYIETTTT
401   EYSSAKMTLD  HYGAYVAQFD  VSWDEFTFDQ  NGKEVLTXKX  WEGSGKDKTA
451   HYSTVIPLPP  NSKNIKIVAR  ECTGLAWEWW  RTIINEQNVP  LTNEIKVSIG
501   GTTLYPTATI  SH
```

FIG. 8F
Putative Cereolysin from Bacillus cereus
Length 500a.a                    gi:418066 (NCBI - D21270)

```
  1   MKNFKGRKFL  TCVLVSLCTL  NYSSISFAET  QAGHANDITK  NASSIDTGIG
 51   NLTYNNQEVL  AVNGDKVESF  VPKESINSNG  KFVVVDVRKN  HLQRHQSIFR
101   LLDSVANRTY  PGAVQLANKA  FADNQPSLLV  AKRKPLNISI  DLPGMRKENT
151   ITVQNPTYGN  VAGAVDDLVS  TWNEKYSATH  TLPARMQYTE  SMVYSKAQIA
201   SALNVNAKYL  DNSLNIDFNA  VANGEKKVMV  AAYKQIFYTV  SAELPNNPSD
251   LFDNSVTFGE  LTRKGVSNSA  PPVMVSNVAY  GRTVYVKLET  TSKSKDVQAA
301   FKALLKNNSV  ETSGQYKDIF  EESTFTAVVL  GGDAKEHNKV  VTKDFNEIRN
351   IIKDNAELSF  KNPAYPISYT  STFLKDNATA  AVHNNTDYIE  TTTTEYSSAK
401   MTLDHYGAYV  AQFDVSWDGF  TFDQNGKEIL  THKTWEGSGK  DKTAHYSTVI
451   PLPPNSKNIK  IVARECTGLA  WEWWRTIIKM  NKMFH
```

FIG. 8G   Ivanolysin O from Listeria ivanovii
Length: 528 AA          gi: 7649482 (CAA42995)

```
  1   MKKIMLLLMT  LLLVSLPLAQ  EAQADASVYS  YQGIISHMAP  PASPPAKPKT
 51   PVEKKNAAQI  DQYIQGLDYD  KNNILVYDGE  AVKNVPPKAG  YKEGNQYIVV
101   EKKKKSINQN  NADIQVINSL  ASLTYPGALV  KANSELVENQ  PDVLPVKRDS
151   VTLSIDLPGM  VNHDNEIVVQ  NATKSNINDG  VNTLVDRWNN  KYSEEYPNIS
201   AKIDYDQEMA  YSESQLVAKF  GAAFKAVNNS  LNVNFGAISE  GKVQEEVINF
251   KQIYYTVNVN  EPTSPSRFFG  KSVTKENLQA  LGVNAENPPA  YISSVAYGRD
301   IFVKLSTSSH  STRVKAAFDA  AFKGKSVKGD  TELENIIQNA  SFKAVIYGGS
351   AKDEVEIIDG  DLSKLRDILK  QGANFDKKNP  GVPIAYTTNF  LKDNQLAVVK
401   NNSEYIETTS  KAYSDGKINL  DHSGAYVARF  NVTWDEVSYD  ANGNEVVEHK
451   KWSENDKDKL  AHFTTSIYLP  GNARNINIHA  KECTGLAWEW  WRTVVDDRNL
501   PLVKNRNVCI  WGTTLYPAYS  DTVDNPIK
```

FIG. 8H   Pyolysin from Arcanobacterium pyogenes
Length: 534  AA     gi: 2252800 (AAC45754)

```
  1   MKRKAFASLV  ASVVAAATVT  MPTASFAAGL  GNSSGLTDGL  SAPRVSISPM
 51   DKVDLKSAQE  TDETSVDKYI  RGLEYDPSGV  LAVKGESIEN  VPVTKDQLKD
101   GTYTVFKHER  KSFNNLRSDI  SAFDANNAHV  YPGALVLANK  DLAKGSPTSI
151   GIARAPQTVS  VDLPGLVDGK  SKVVINNPTK  SSVTQGMNGL  LDGWIQRNSK
201   YPDHAAKIFY  DETMVTSKRQ  LEAKFGLGFE  KVSAKLNVDF  DAIHKRERQV
251   AIASFKQIYY  TASVDTPTSP  HSVFGPNVTA  QDLKDRGVNN  KNPLGYISSV
301   SYGRQIFVKL  ETTSTSNDVQ  AAFSGLFKAK  FGNLSTEFKA  KYADILNKTR
351   ATVYAVGGSA  RGGVEVATGN  IDALKKIIKE  ESTYSTKVPA  VPVSYSVNFL
401   KDNQLAAVRS  SGDYIETTAT  TYKSGEITFR  HGGGYVAKFG  LKWDEISYDP
451   QGKEIRTPKT  WSGNWVGRTL  GFRETIQLPA  NARNIHVEAG  EATGLAWDPW
501   WTVINKKNLP  LVPHREIVLK  GTTLNPWVEE  NVKS
```

FIG. 8I

Seeligeriolysin O from Listeria seeligeri
Length: 530 AA                    gi: 44145 (CAA42996)

```
  1  MKIFGLVIMS LLFVSLPITQ QPEARDVPAY DRSEVTISPA ETPESPPATP
 51  KTPVEKKHAE EINKYIWGLN YDKNSILVYQ GEAVTNVPPK KGYKDGSEYI
101  VVEKKKKGIN QNNADISVIN AISSLTYPGA LVKANRELVE NQPNVLPVKR
151  DSLTLSVDLP GMTKKDNKIF VKNPTKSNVN NAVNTLVERW NDKYSKAYPN
201  INAKIDYSDE MAYSESQLIA KFGTAFKAVN NSLNVNFEAI SDGKVQEEVI
251  SFKQIYYNIN VNEPTSPSKF FGGSVTKEQL DALGVNAENP PAYISSVAYG
301  RQVYVKLSSS SHSNKVKTAF EAAMSGKSVK GDVELTNIIK NSSFKAVIYG
351  GSAKEEVEII DGNLGELRDI LKKGSTYDRE NPGVPISYTT NFLKDNDLAV
401  VKNNSEYIET TSKSYTDGKI NIDHSGGYVA QFNISWDEVS YDENGNEIKV
451  HKKWGENYKS KLAHFTSSIY LPGNARNINI YARECTGLFW EWWRTVIDDR
501  NLPLVKNRNV SIWGTTLYPR HSNNVDNPIQ
```

FIG. 8J

Streptolysin O from S. pyogenes
Length: 574 AA                    gi: 19747435 (AAL96968)

```
  1  MKDMSNKKTF KKYSRVAGLL TAALIIGNLV TANAESNKQN TASTETTTTN
 51  EQPKPESSEL TTEKAGQKTD DMLNSNDMIK LAPKEMPLES AEKEEKKSED
101  KKKSEEDHTE EINDKIYSLN YNELEVLAKN GETIENFVPK EGVKKADKFI
151  VIERKKKNIN TTPVDISIID SVTDRTYPAA LQLANKGFTE NKPDAVVTKR
201  NPQKIHIDLP GMGDKATVEV NDPTYANVST AIDNLVNQWH DNYSGGNTLP
251  ARTQYTESMV YSKSQIEAAL NVNSKILDGT LGIDFKSISK GEKKVMIAAY
301  KQIFYTVSAN LPNNPADVFD KSVTFKELQR KGVSNEAPPL FVSNVAYGRT
351  VFVKLETSSK SNDVEAAFSA ALKGTDVKTN GKYSDILENS SFTAVVLGGD
401  AAEHNKVVTK DFDVIRNVIK DNATFSRKNP AYPISYTSVF LKNNKIAGVN
451  NRTEYVETTS TEYTSGKINL SHRGAYVAQY EILWDEINYD DKGKEVITKR
501  RWDNNWYSKT SPFSTVIPLG ANSRNIRIMA RECTGLAWEW WRKVIDERDV
551  KLSKEINVNI SGSTLSPYGS ITYK
```

FIG. 8K  Suilysin from Streptococcus suis

Length: 497 AA          gi: 30088598 (AAN34600)

```
  1 MRKSSHLILS SIVSLALVGV TPLSVLADSK QDINQYFQSL TYEPQEILTN
 51 EGEYIDNPPA TTGMLENGRF VVLRREKKNI TNNSADIAVI DAKAANIYPG
101 ALLRADQNLL DNNPTLISIA RGDLTLSLNL PGLANGDSHT VVNSPTRSTV
151 RTGVNNLLSK WNNTYAGEYG NTQAELQYDE TMAYSMSQLK TKFGTSFEKI
201 AVPLDINFDA VNSGEKQVQI INFKQIYYTV SVDEPESPSK LFAEGTTVED
251 LQRNGITDEV PPVYVSSVSY GRSMFIKLET SSRSTQVQAA FKAAIKGVDI
301 SGNAEYQDIL KNTSFSAYIF GGDAGSAATV VSGNIETLKK IIEEGARYGK
351 LNPGVPISYS TNFVKDNRPA QILSNSEYIE TTSTVHNSSA LTLDHSGAYV
401 AKYNITWEEV SYNEAGEEVW EPKAWDKNGV NLTSHWSETI QIPGNARNLH
451 VNIQECTGLA WEWWRTVYDK DLPLVGQRKI TIWGTTLYPQ YADEVIE
```

FIG. 8L  Tetanolysin from Clostridium tetani

Length: 527 AA          gi: 28211522 (NP782466)

```
  1 MNKNVLKFVS RSLLIFSMTG LISNYNSSNV LAKGNVEEHS LINNGQVVTS
 51 NTKCNLAKDN SSDIDKNIYG LSYDPRKILS YNGEQVENFV PAEGFENPDK
101 FIVVKREKKS ISDSTADISI IDSINDRTYP GAIQLANRNL MENKPDIISC
151 ERKPITISVD LPGMAEDGKK VVNSPTYSSV NSAINSILDT WNSKYSSKYT
201 IPTRMSYSDT MVYSQSQLSA AVGCNFKALN KALNIDFDSI FKGEKKVMLL
251 AYKQIFYTVS VDPPNRPSDL FGDSVTFDEL ALKGINNNNP PAYVSNVAYG
301 RTIYVKLETT SKSSHVKAAF KALINNQDIS SNAEYKDILN QSSFTATVLG
351 GGAQEHNKII TKDFDEIRNI IKNNSVYSPQ NPGYPISYTT TFLKDNSIAS
401 VNNKTEYIET TATEYTNGKI VLDHSGAYVA QFQVTWDEVS YDEKGNEIVE
451 HKAWEGNNRD RTAHFNTEIY LKGNARNISV KIRECTGLAW EWWRTIVDVK
501 NIPLAKERTF YIWGTTLYPK TSIETKM
```

FIG. 8M
Listeriolysin O from Listeria monocytogenes
Length: 529 AA          gi: 7595976   (AAF64524)

```
  1   MKKIMLVFIT LILISLPIAQ QTEAKDASAF HKEDLISSMA PPTSPPASPK
 51   TPIEKKHADE IDKYIQGLDY NKNNVLVYHG DAVTNVPPRK GYKDGNEYIV
101   VEKKKKSINQ NNADIQVVNA ISSLTYPGAL VKANSELVEN QPDVLPVKRD
151   SLTLSIDLPG MTNQDNKIVV KNATKSNVNN AVNTLVERWN EKYAQAYPNV
201   SAKIDYDDEM AYSESQLIAK FGTAFKAVNN SLNVNFGAIS EGKMQEEVIS
251   FKQIYYNVNV NEPTRPSRFF GKAVTKEQLQ ALGVNAENPP AYISSVAYGR
301   QVYLKLSTNS HSTKVKAAFD AAVSGKSVSG DVELTNIIKN SSFKAVIYGG
351   SAKDEVQIID GNLGDLRDIL KKGATFNRET PGVPIAYTTN FLKDNELAVI
401   KNNSEYIETT SKAYTDGKIN IDHSGGYVAQ FNISWDEINY DPEGNEIVQH
451   KNWSENNKSK LAHFTSSIYL PGNARNINVY AKECTGLAWE WWRTVIDDRN
501   LPLVKNRNIS IWGTTLYPKY SNSVDNPIE
```

FIG. 8N
Thuringiolysin from Bacillus thuringiensis
Length: 512 AA          gi: 49481660  (YP_037419.1; NC_005957.1)

```
  1   MIFLNIKKNG KRRKFLTCVL VSLCTLNYSS TSFAETQAGH ATDITKNASS IDTGIGNLTY
 61   NNQEVLAVNG DKVESFVPKE SINSNGKFVV VEREKKSLTT SPVDISIIDS VANRTYPGAV
121   QLANKAFADN QPSLLVAKRK PLNISIDLPG MRKENTITVQ NPTYGNVAGA VDDLVSTWNE
181   KYSETHTLPA RMQYTESMVY SKSQIASALN VNAKYLDNSL NIDFNAVANG EKKVMVAAYK
241   QIFYTVSAEL PNNPSDLFDN SVTFDELTRK GVSNSAPPVM VSNVAYGRTV YVKLETTSKS
301   KDVQAAFKAL LKNNSVETSG QYKDIFEEST FTAVVLGGDA KEHNKVVTKD FNEIRNIIKD
361   NAELSFKNPA YPISYTSTFL KDNATAAVHN NTDYIETTTT EYSSAKMTLD HYGAYVAQFD
421   VSWDEFTFDQ NGKEVLTHKT WEGSGKDKTA HYSTVIPLPP NSKNIKIVAR ECTGLAWEWW
481   RTIINEQNVP LTNEIKVSIG GTTLYPTASI SH
```

ADJUVANT COMPOUNDS

The present application is §371 application of PCT/GB2007/002242 filed 15 Jun. 2007 which claims priority to U.S. Provisional Application No. 60/813,826 filed 15 Jun. 2006, the entire disclosures of each being incorporated herein by reference.

FIELD OF THE INVENTION

The invention relates to immunogenic compositions. In particular it relates to compositions for raising prophylactic or therapeutic immune responses against desired antigens, such as vaccine compositions.

BACKGROUND TO THE INVENTION

Local immune responses at mucosal surfaces are thought to be important in combating infection to many bacteria, viruses and parasites, which gain access to the host through these surfaces. However, stimulation of local immune responses with purified non-replicating antigens is difficult. In fact, the healthy immune system appears tolerant to non-living antigens when they are presented at mucosal surfaces. This has seriously inhibited the development of new vaccines that can be delivered mucosally. To date, only a few proteins have been identified which activate strong local and systemic immune responses following mucosal presentation. Of these, the highly homologous enterotoxins, Cholera toxin (CT) from *Vibrio cholerae* and heat labile toxin from enterotoxigenic *E. coli*-(LT) have been studied extensively [1, 2]. In addition to the generation of strong anti-toxin responses, these proteins are able to activate immune responses to normally non-immunogenic co-administered antigen [3]. The adjuvant activity of these toxins has been studied extensively in animal models. Their high toxicity, however, makes them impractical for use in humans.

To circumvent the toxicity problem, site directed mutants of these toxins have been engineered which are no longer enzymatically active but which retain adjuvant activity [4-7]. It is hoped that these non-toxic derivatives will be suitable for inclusion in new vaccine formulations. A number of such mutant toxins have been constructed and characterised. This work has helped to establish a structure/function relationship between adjuvant activity of these proteins and the holotoxin formation [8]. However, little time and effort has been spent on the identification of alternative adjuvants.

Pneumolysin produced by *Streptococcus pneumoniae* is a pore forming protein produced by the majority of the disease causing serotypes. Vaccination with this protein has been shown to elicit some protective effects in animal models of infection.

Pneumolysin has at least two major activities important in its role in pathogenesis: the ability to form pores and the ability to activate the complement pathway. The functional regions for these activities have been located within the molecule and both activities have been shown to be important in the causation of disease [9]. The toxin is important in the pathogenesis of meningitis as it can cause damage to the ependymal cilia of the brain [10] and can induce apoptosis of brain cells [11]. The neurotoxicity of pneumolysin has been shown to be due to alterations in calcium flux into cells and signalling via activation of the p38 MAP kinase [11, 12]. Pneumolysin has recently been shown to bind to Toll-like receptor 4 (TLR-4) [13]. This interaction with TLR-4 was essential for the protection of mice against invasive disease caused by the pneumococcus. Pneumolysin therefore plays a diverse and important role in the pathogenesis of pneumococcal infections.

Listeriolysin O has previously been used to deliver heterologous antigen peptides to the MHC class I antigen presentation pathway in order to stimulate cytotoxic T cell responses against the heterologous antigen. In this system, nucleic acids encoding the listeriolysin O protein fused to the heterologous antigen (e.g. a tumour-specific antigen or viral antigen) were administered directly to the subject as DNA vaccines, or used to transform the intracellular bacteria *Listeria monocytogenes* which were themselves used as live vaccines. In either case, it is believed that the fusion protein is produced within the vaccinated subject's own cells (either by the cells themselves, or by the infecting bacteria), degraded in the usual manner, and presented to the immune system via MHC class I molecules. See [14] and references cited therein.

SUMMARY OF THE INVENTION

The present inventors have now found that cytolysin proteins possess adjuvant activity in their own right when administered in conjunction with other peptide antigens.

Accordingly, in its broadest form, the present invention provides the use of a cytolysin protein as an adjuvant, when administered in conjunction with a heterologous peptide antigen, in particular when administered as a fusion with the heterologous peptide antigen.

In one aspect, the invention provides a method of generating an immune response against a peptide antigen, comprising administering to a subject a fusion protein comprising said peptide antigen and a cytolysin.

The invention further provides the use of a fusion protein comprising a peptide antigen and a cytolysin in the preparation of a medicament for the generation of an immune response against the peptide antigen.

The invention further provides a fusion protein comprising a peptide antigen and a cytolysin, for use in the generation of an immune response against the peptide antigen.

The invention also provides an immunogenic composition comprising a fusion protein and a pharmaceutically acceptable carrier, wherein the fusion protein comprises a peptide antigen and a cytolysin.

The invention further provides a fusion protein comprising a peptide antigen and a cytolysin for use in a method of medical treatment.

The compositions and methods of the invention are used for generating an immune response in a subject against a target peptide antigen. The subject is typically a mammal, for example, a primate (e.g. Old World monkey, New World monkey, great ape or human), rodent (e.g. mouse or rat), canine (e.g. domestic dog), feline (e.g. domestic cat), equine (e.g. horse), bovine (e.g. cow), caprine (e.g. goat), ovine (e.g. sheep) or lagomorph (e.g. rabbit).

As well as administering the fusion protein directly, it is also possible to use so-called "DNA vaccination" techniques, wherein a nucleic acid encoding the fusion protein is administered to the subject such that the nucleic acid is taken up by the subject's own cells and the fusion protein is expressed by those cells from the nucleic acid. In general, it will be desirable for the fusion protein to be secreted from the cells in which it is synthesised. This may allow the fusion protein to enter the subject's system and exert a similar effect to a fusion protein which has been administered directly. Without wishing to be bound by theory, this may include uptake and presentation of the target antigen and/or the cytolysin by antigen presenting cells via the MHC class II pathway.

Thus the invention further provides a method of generating an immune response against a peptide antigen, comprising administering to a subject a nucleic acid encoding a fusion protein, wherein the fusion protein comprises said peptide antigen and a cytolysin, and wherein the fusion protein is secreted from a cell of the subject when expressed within said cell.

The subject is typically a mammal, as described above.

The invention further provides the use of a nucleic acid encoding a fusion protein in the preparation of a medicament for the generation of an immune response against a peptide antigen, wherein the fusion protein comprises the peptide antigen and a cytolysin, and wherein the fusion protein is secreted from a mammalian cell when expressed within said cell.

The invention further provides a nucleic acid encoding a fusion protein for use in the generation of an immune response against a peptide antigen, wherein the fusion protein comprises a peptide antigen and a cytolysin, and wherein the fusion protein is secreted from a mammalian cell when expressed within said cell.

The invention also provides an immunogenic composition comprising a nucleic acid encoding a fusion protein and a pharmaceutically acceptable carrier, wherein the fusion protein comprises a peptide antigen and a cytolysin, and wherein the fusion protein is secreted from a mammalian cell when expressed within said cell.

The invention further provides a nucleic acid encoding a fusion protein, wherein the fusion protein comprises a peptide antigen and a cytolysin, and wherein the fusion protein is secreted from a mammalian cell when expressed within said cell.

The nucleic acid may be, provided as part of an expression vector, and/or within a cell capable of expressing and secreting the fusion protein. The invention therefore provides an expression vector comprising a nucleic acid as described above. The invention also provides a cell comprising a nucleic acid or an expression vector as described above.

The invention further provides the use of a cell or expression vector for the generation of an immune response against a peptide antigen, comprising administering such a cell or expression vector to a subject.

The invention further provides the use of a cell or expression vector as described in the preparation of a medicament for the generation of an immune response against a peptide antigen.

The invention further provides a cell or expression vector as described, for use in the generation of an immune response against the peptide antigen.

The invention also provides an immunogenic composition comprising a cell or expression vector as described and a pharmaceutically acceptable carrier.

The invention further provides a cell or expression vector as described for use in a method of medical treatment.

The immune response may be generated for prophylaxis or therapy of any condition in which it is beneficial to the subject to mount an immune response against a target antigen. Such conditions include, but are not limited to, infection by an infectious organism, and also include the treatment of cancer. For example, in the treatment of cancer, it may be desirable to induce or increase an immune response to a marker expressed specifically or preferentially on cancer cells. Such markers are often referred to as tumour-specific markers, although their expression is not restricted to solid tumours. Infectious organisms include intracellular and extracellular bacteria, viruses, fungi, and other parasites such as malaria parasites.

The target antigen (i.e. the antigen against which it is desirable to generate an immune response) is a peptide antigen. The term "peptide" refers to the nature of the antigen, i.e. that it is formed from amino acids linked by peptide bonds, and should not be taken to imply any particular size or length. Typically the peptide antigen will be at least 8 amino acids in length, and may be up to 50 amino acids in length, up to 100 amino acids, up to 200 amino acids, or even longer.

Without wishing to be bound by any particular theory, the peptide antigen, when not fused to the cytolysin protein, should be capable of binding to a MHC class II molecule, or should be capable of being processed within an antigen-presenting cell to give rise to one or more peptides capable of binding to a MHC class II molecule.

The target peptide antigen may be from any source and is provided in a fusion protein with the cytolysin. Thus the fusion protein is a single chain of amino acids containing the sequence of a cytolysin molecule (or a fragment thereof having adjuvant activity—see below) and a peptide antigen which is not part of the same peptide chain as the cytolysin protein in nature.

In the fusion protein, the cytolysin may be N-terminal of the peptide antigen. Alternatively, the peptide antigen may be N-terminal of the cytolysin. The fusion protein may comprise other protein components, such as a linker peptide between the peptide antigen and the cytolysin, or a peptide tag for affinity purification (for example at the N- or C-terminus of the molecule).

In general, the peptide antigen is heterologous to the cytolysin; that is to say, it is not the cytolysin protein itself or a fragment thereof. (Although in certain circumstances it may be desirable to use a fusion protein comprising two copies of the same cytolysin, e.g. in order to induce a response to the cytolysin protein itself.) The target antigen may be a complete protein, an isolated domain of a protein, or a peptide fragment of a protein. It may be derived from the same organism as the cytolysin. When the antigen is from a species which produces a cytolysin, it may be desirable to use the cytolysin from that species, as any immune response which is generated against the cytolysin itself will contribute to the protection afforded against that organism. For example, when the cytolysin is pneumolysin, the antigen may be an antigen from *S. pneumoniae*, such as PsaA (Pneumococcal surface antigen A) or a fragment thereof. However, it may be from a different organism, and in various embodiments, the target peptide antigen is derived from an organism which does not express a cytolysin.

The target antigen may be derived from an infectious organism, including a bacterium, fungus, virus or other parasite, such as a malarial parasite. In alternative embodiments, the target antigen may be derived from the same species as the subject to which it is to be administered. For example, it may be derived from a protein expressed on a cancer cell (e.g. a tumour-specific marker, as mentioned above). In such cases, the target peptide antigen may be derived from the subject to whom the fusion protein is to be administered.

In particular, the fusion proteins described herein (and the nucleic acids encoding them) may be used to generate (or enhance generation of) serum antibodies against the target antigen, or against the protein from which the target antigen is derived. The serum antibodies produced are typically IgG, and may include IgG1.

Administration may be by any suitable route, and may be oral or parenteral. Because of the difficulties experienced with oral delivery of peptide agents, parenteral administration may prove the most suitable. Suitable parenteral routes include but are not limited to intravenous, intramuscular, intraperitoneal, cutaneous, subcutaneous, transdermal, and other mucosal routes such as nasal, buccal, rectal and vaginal routes.

As well as stimulating serum antibody production against a target antigen, the inventors have found that cytolysin proteins have the ability to stimulate production of a mucosal immune response against the associated target peptide antigen. It is well-known in the art that it is difficult to reliably generate mucosal immune responses. Presentation of non-living antigens at mucosal surfaces often induces tolerance, rather than immunity. However, mucosal immune responses are desirable, as they form a first line of defense against those types of infectious organism which gain access to the body-via—the mucosa. Mucosal immune response are typically characterised by the production of IgA at the relevant mucosal surfaces.

In order to generate a mucosal immune response, mucosal administration may be used (i.e. such that the fusion protein is taken up through a mucosal surface). Any suitable mucosal route may be applied, including nasal, buccal, rectal, vaginal or oral (for uptake through the intestinal mucosa). Nasal administration may be particularly convenient.

Any cytolysin may be used in the methods and compositions of the invention. Examples include pneumolysin from *Streptococcus pneumoniae*, perfringolysin O from *Clostridium perfringens*, intermedilysin from *Streptococcus intermedius*, alveolysin from *Bacillus alvei*, anthrolysin from *Bacillus anthracia*, putative cereolysin from *Bacillus cereus*, ivanolysin O from *Listeria ivanovii*, pyolysin from *Arcanobacterium pyogenes*, seeligeriolysin O from *Listeria seeligeri*, streptolysin O from *S. pyogenes*, suilysin from *Streptococcus suis*, tetanolysin from *Clostridium tetani*, listeriolysin O from *Listeria monocytogenes*, streptolysin O from *Streptococcus equisimilis*, streptolysin O from *S. canis*, thuringiolysin O from *Bacillus thuringiensis*, latersporolysin O from *B. latersporus*, botulinolysin from *Clostridium botulinum*, chauveolysin from *C. chauvoei*, bifermentolysin from *C. bifermentans*, sordellilysin from *C. sordellii*, histolyticolysin from *Clostridium histiolyticum*, novylysin from *Clostridium novyi* and septicolysin O from *Clostridium septicum*.

Cytolysin mutants may also be used. Particularly suitable mutants are those described in WO2005/108419 and WO2005/108580 which possess a mutation (e.g. a deletion or substitution) of one or more amino acids within the region corresponding to amino acids 144 to 161 of the wild type pneumolysin sequence which reduces haemolytic activity and/or oligomerisation activity relative to the wild type cytolysin protein.

Thus the mutant cytolysin may differ from the wild type protein by the presence of a mutation (e.g. a deletion or substitution) within the region corresponding to amino acids 144 to 151 of the wild type pneumolysin sequence.

For example, an amino acid corresponding to alanine 146 of pneumolysin may be substituted or deleted.

The mutant protein may differ from the wild type protein by the deletion of two adjacent amino acids within the region corresponding to amino acids 144 to 151 of the wild type pneumolysin sequence.

For example, amino acids corresponding to valine 144 and proline 145 of pneumolysin, or corresponding to alanine 146 and arginine 147 of pneumolysin, or corresponding to methionine 148 and glutamine 149 of pneumolysin, or corresponding to tyrosine 150 and glutamic acid 151 of pneumolysin may be deleted.

Additionally or alternatively, the mutant may possess a substitution at a position corresponding to position 181 in wild-type perfringolysin sequence. For example, the mutant may carry a substitution equivalent to Y181A in wild-type perfringolysin.

Additionally or alternatively, the mutant may possess at least one amino acid substitution or deletion in at least one of the regions corresponding to amino acids 257-297, 367-397 or 424-437 of the wild type pneumolysin sequence which reduces haemolytic activity relative to the wild type protein. Preferred positions include those corresponding to amino acids 367, 384, 385, 428, 433 and 435 of the pneumolysin sequence. In such cases, the mutant may be a mutant of pneumolysin.

Additionally or alternatively, the mutant may comprise at least one mutation in the region corresponding to amino acids 368 to 397 of wild-type pneumolysin which reduces complement-activating activity relative to the wild type cytolysin. For example, the mutant may comprise a substitution or deletion at a residue corresponding to positions 384 or 385 of wild type pneumolysin.

DESCRIPTION OF THE FIGURES

FIG. 8A-FIG. 8N: Amino acid sequences of selected wild-type cytolysin polypeptides. FIG. 8A. Pneumolysin from *Streptococcus pneumoniae* (SEQ ID NO: 25); FIG. 8B. Perfringolysin O from *Clostridium perfringens* (SEQ ID NO: 26); FIG. 8C. Intermedilysin from *Streptococcus intermedius* (SEQ ID NO: 27); FIG. 8D. Alveolysin from *Bacillus alvei* (SEQ ID NO: 28); FIG. 8E. Anthrolysin from *Bacillus anthracis* (SEQ ID NO: 29); FIG. 8F. Putative Cereolysin from *Bacillus cereus* (SEQ ID NO: 30); FIG. 8G. Ivanolysin O from *Listeria ivanovii* (SEQ ID NO: 31); FIG. 8H. Pyolysin from *Arcanobacterium pyogenes* (SEQ ID NO: 32); FIG. 8I. Seeligeriolysin O from *Listeria seeligeri* (SEQ ID NO: 33); FIG. 8J. Streptolysin O from *S. pyogenes* (SEQ ID NO: 34); FIG. 8K. Suilysin from *Streptococcus suis* (SEQ ID NO: 35); FIG. 8L. Tetanolysin from *Clostridium tetani* (SEQ ID NO: 36); FIG. 8M. Listeriolysin O from *Listeria monocytogenes* (SEQ ID NO: 37); FIG. 8N. Thuringiolysin from *Bacillus*

*thuringiensis* (SEQ ID NO: 38) (previously annotated as perfringolysin). All accession numbers are derived from NCBI-GenBank Flat File Release 141.0, Apr. 15, 2004, apart from apart from those of thuringiolysin which are from NCBI-GenBank Flat File Release 153.0, Apr. 15, 2006.

Figure 9:
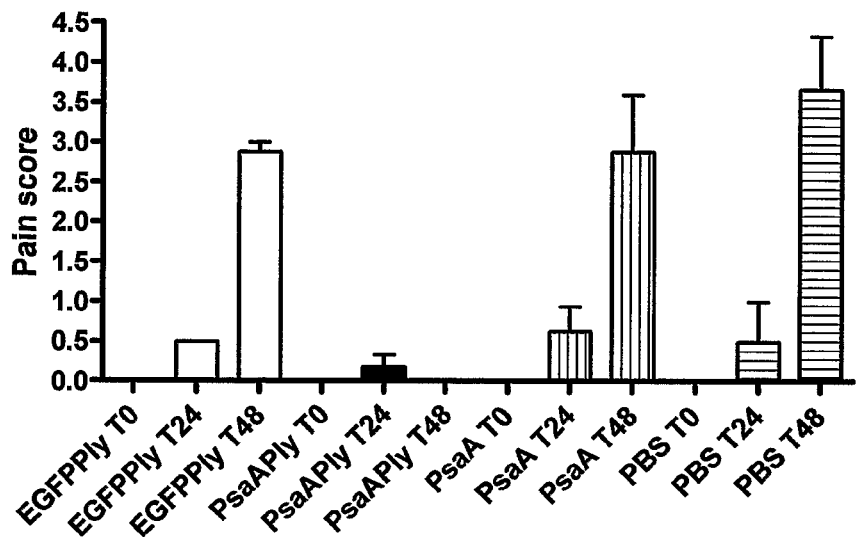

FIG. 9: Pain scores at 0, 24 and 48 hours after inoculation with *S. pneumoniae*. Challenge with *S. pneumoniae* took place at least 4 weeks after final immunisation with the specified vaccination combinations.

Figure 10:
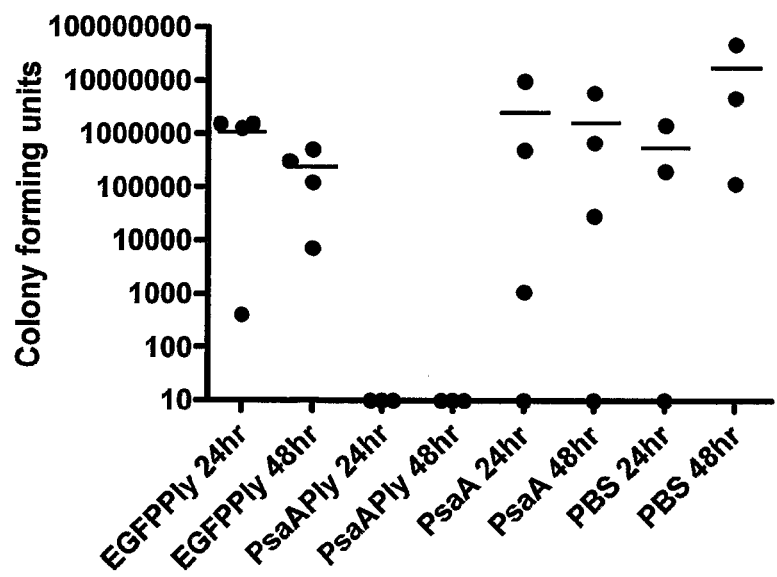

FIG. 10: Bacterial load in blood determined at 24 and 48 hours after inoculation with *S. pneumoniae*.

DETAILED DESCRIPTION OF THE INVENTION

Cytolysins

Cytolysins are cholesterol-binding toxin molecules produced by a number of types of bacteria. They bind to cholesterol in host cell membranes and oligomerise to form large 30- to 50-member ring structures which form lytic pores in the host cell membrane (see e.g. Palmer, M. (2001) *Toxicon* 39:1681-1689; Jedrzejas, M J, Microbiol Mol Biol Rev. 2001 June; 65(2):187-207). As a result, cytolysins display haemolytic activity against red blood cells.

Thus, a cytolysin is a molecule which, in the wild-type state, is capable of binding to membrane cholesterol molecules, and has the ability to oligomerise and form pores in cholesterol-containing membranes.

The amino acid sequences of a number of wild type cholesterol-binding cytolysins (CBCs) are shown in FIG. 8. FIG. 8 also indicates the GenBank identification number for each sequence. The methods and compositions described in this specification are not restricted to the cytolysins shown in FIG. 8, but encompass use of any cholesterol-binding cytolysin.

Wild type cytolysin molecules may be used, particularly for veterinary use. However, in the eventuality that a wild type cytolysin molecule is unacceptable or disadvantageous for any reason (e.g. unacceptably toxic for human use), it is possible to use a cytolysin mutant comprising one or more mutations which affect one or more biological activities of the cytolysin such as haemolytic activity, ability to oligomerise, or ability to activate complement.

For example, WO2005/108419 and WO2005/108580 disclose cytolysin mutants having a mutation (e.g. a substitution or deletion) within the region corresponding to amino acids 144 to 161 of the wild type pneumolysin protein. These mutants have reduced haemolytic activity and/or oligomerisation as compared to the wild type cytolysins, and therefore are less toxic. The reduction in oligomerisation activity also improves their suitability for use in a therapeutic product by reducing their tendency to aggregate when formulated into a medicament.

The regions of the cytolysins shown in FIG. 8 corresponding to residues 144 to 161 of wild-type pneumolysin are listed below. The amino acid sequences provided are SEQ ID NOs: 1-14, from top to bottom.

| Cholesterol Binding Cytolysin | Consensus sequence to PLY (a.a. 144-161) | Amino acid position |
|---|---|---|
| Pneumolysin | VPARMQYEKITAHSMEQL | V144-L161 |
| Perfringolysin O | LPARTQYSESMVYSKSQI | L175-I192 |
| Seeligeriolysin | INAKIDYSDEMAYSESQL | I201-L218 |
| Septicolysin | LPARTQYSESMVYSKSQI | L173-I190 |
| Streptolysin O | LPARTQYTESMVYSKSQI | L249-I266 |
| Intermedilysin | VPARMQYESISAQSMSQL | V202-L219 |
| Alveolysin | LPARLQYAESMVYSQNQI | L177-I194 |
| Anthrolysin | LPARTQYSESMVYSKSQL | L188-L205 |
| Cereolysin | LPARTQYSESMVYSKSQI | L175-I192 |
| Ivanolysin | ISAKIDYDQEMAYSESQL | I199-L216 |
| Suilysin | TQAELQYDETMAYSMSQL | T172-L189 |
| Tetanolysin | IPTRMSYSDTMVYSQSQL | I201-L218 |
| Listeriolysin O | VSAKIDYDDEMAYSESQL | V200-L217 |
| Thuringiolysin | LPARMQYTESMVYSKSQI | L188-I205 |

The mutant may have a substitution or deletion of one or more amino acids within the region corresponding to amino acids 144 to 161, e.g. 144 to 151 of the wild type pneumolysin sequence. Among the cytolysins shown in FIG. 8, the consensus sequence of the region corresponding to amino acids 144 to 151 of the wild type pneumolysin sequence is VPARMQYE (SEQ ID NO: 15).

Thus, the mutant cytolysin may have a mutation, e.g. a substitution or deletion, at one or more of the amino acid residues corresponding to amino acids 144, 145, 146, 147, 148, 149, 150, 151, 152, 153, 154, 155, 156, 157, 158, 159, 160 or 161 of wild type pneumolysin.

Certain preferred mutant cytolysin proteins differ from the wild type protein by the substitution or deletion of two adjacent amino acids within the region corresponding to amino acids 144 to 151 of the wild type pneumolysin sequence. Examples of such double mutants are those which contain substitutions or deletions of amino acids corresponding to valine 144 and proline 145, alanine 146 and arginine 147, methionine 148 and glutamine 149, or tyrosine 150 and glutamic acid 151, i.e. the corresponding amino acids shown in the table above.

The mutant may have a substitution at a residue corresponding to Y181 of perfringolysin. This residue corresponds to Y150 of pneumolysin. Such mutants may be derived from perfringolysin, or from other cytolysin proteins.

Further mutants of cytolysins having reduced haemolytic activity are described in WO 90/06951, and contain at least one amino acid substitution or deletion in at least one of the regions corresponding to amino acids 257-297, 367-397 or 424-437 of the wild type pneumolysin sequence, and in particular at positions corresponding to amino acids 367, 384, 385, 428, 433 and 435 of the pneumolysin sequence. Thus the cytolysin protein used in the methods and compositions described herein may comprise one or more such mutations in addition to, or instead of, the mutation in the region corresponding to amino acids 144-161 of the pneumolysin sequence.

Mutations reducing the ability to activate complement may be made, for example, in the region corresponding to amino acids 368 to 397 of wild-type pneumolysin, and in particular at residues corresponding to positions 384 (Tyr) and 385 (Asp) of wild type pneumolysin. Such mutations are described by Mitchell, T. J. et al, *Complement Activation and*

*Antibody Binding by Pneumolysin via a Region of the Toxin Homologous to a Human Acute-Phase Protein.* Molecular Microbiology, 1991. 5(8): p. 1883-1888.

The cytolysin proteins may comprise other mutations relative to the sequences shown in FIG. 8. These mutations may themselves reduce one or more biological activities of the cytolysin protein, such as the haemolytic activity, the oligomerisation activity, or the ability to activate complement, or they may be phenotypically silent.

Deletions and substitutions are examples of mutations which may be used to provide the mutant proteins of the invention with reduced toxicity. Non-conservative substitutions may be particularly suitable for reducing toxicity of the mutant, as a mutant having a non-conservative mutation is less likely to retain wild-type levels of function than one having a conservative substitution.

A conservative substitution may be defined as a substitution within an amino acid class and/or a substitution that scores positive in the BLOSUM62 matrix as shown below, thus a non-conservative substitution may be defined as a substitution between amino acid classes, or which does not score positive in the BLOSUM62 matrix.

According to one classification, the amino acid classes are acidic, basic, uncharged polar and nonpolar, wherein acidic amino acids are Asp and Glu; basic amino acids are Arg, Lys and H is; uncharged polar amino acids are Asn, Gln, Ser, Thr and Tyr; and non-polar amino acids are Ala, Gly, Val, Leu, Ile, Pro, Phe, Met, Trp and Cys.

According to another classification, the amino acid classes are small hydrophilic, acid/acidamide/hydrophilic, basic, small hydrophobic and aromatic, wherein small hydrophilic amino acids are Ser, Thr, Pro, Ala and Gly; acid/acidamide/hydrophilic amino acids are Asn, Asp, Glu and Gln; basic amino acids are H is, Arg and Lys; small hydrophobic amino acids are Met, Ile, Leu and Val; and aromatic amino acids are Phe, Tyr and Trp.

Conservative substitutions, which score positive in the BLOSUM62 matrix, are as follows:

the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Percent (%) amino acid similarity is defined in the same way as identity, with the exception that residues scoring a positive value in the BLOSUM62 matrix are counted. Thus, residues which are non-identical but which have similar properties (e.g. as a result of conservative substitutions) are also counted.

References in this specification to an amino acid of a first sequence "corresponding to" an amino acid of a second sequence should be construed accordingly. That is to say, residues which align with one another when the two sequences are aligned as described above, can be considered to correspond to one another.

Fragments of wild-type or mutant cytolysin proteins which retain adjuvant activity may also be used. Such fragments may be, for example, at least 50 amino acids in length, at least 100 amino acids in length, at least 200 amino acids in length, at least 300 amino acids in length, or at least 400 amino acids in length, as long as they retain adjuvant activity. The term "cytolysin" or the name of any specific cytolysin should be construed to include such functional fragments unless the context demands otherwise.

| | Original Residue | | | | | | | | | | | | | | | | | | |
|---|---|---|---|---|---|---|---|---|---|---|---|---|---|---|---|---|---|---|---|
| | C | S | T | P | A | G | N | D | E | Q | H | R | K | M | I | L | V | F | Y | W |
| Substitution | — | T | S | — | S | — | S | N | D | E | N | Q | E | I | M | M | M | Y | H | F |
| | | A | | | | | D | E | Q | R | Y | K | Q | L | L | I | I | W | F | Y |
| | | N | | | | | H | | K | K | | | R | V | V | V | L | | W | |

Amino acid insertions within the region of amino acids 144 to 161, e.g. 144 to 151, may also be used to reduce toxicity of the PLY mutant. For example, insertions of 1, 2, 3, 4, 5, 10, 15, 20 or more amino acids may be used. However, deletions and substitutions are generally preferred to insertions as they are less likely to disrupt the wild type epitope; such disruption could reduce the immunogenicity of the mutant protein, which may be undesirable if the immunogenic composition is intended to generate an immune response against the bacterium which produces the wild-type cytolysin.

The cytolysin protein preferably has at least 80% amino acid identity with the corresponding wild type sequence, e.g. as shown in FIG. 8. The mutant may have at least 85% identity, at least 90% identity, or at least 95% identity with the wild type sequence.

Percent (%) amino acid sequence identity with respect to a reference sequence is defined as the percentage of amino acid residues in a candidate sequence that are identical with the amino acid residues in the reference sequence, after aligning Adjuvant Activity The methods and compositions described in this specification are capable of stimulating immune responses against a target peptide antigen; that is to say, enhancing a pre-existing immune response against the antigen, or generating a response de novo.

In particular, the methods and compositions of the present invention may be used to stimulate serum immunoglobulin production against the target peptide antigen. The serum immunoglobulin typically comprises, or consists primarily of, IgG.

Additionally or alternatively, the methods and compositions of the present invention may be used to stimulate mucosal immunity against the target peptide antigen. Mucosal immunity is normally characterised by the production of IgA, but may also involve activation of lymphocytes in mucosal-associated lymphoid tissue.

This is in contrast to the methods described by Singh et al. [14] which are intended to generate cytotoxic T cells capable of killing cells expressing the target antigen.

Without wishing to be bound by any particular theory, the difference in effect may be due to the different mechanisms of presentation of the target antigen in the two systems.

In general, immune responses which favour generation of serum antibodies against a target antigen are often described as Th2-type responses. In Th2 responses, T cell proliferation is biased towards CD4$^+$T cell proliferation. Cytokine production is biased towards production of one or more of IL-3, IL-4, IL-5, IL-6 and IL-13, rather than interferon gamma and IL-2. Normally, such responses are believed to result from presentation of the target antigen by professional antigen presenting cells (such as B cells, macrophages and dendritic cells) in the context of MHC class II molecules. The antibodies generated may include the IgG1 isotype.

By contrast, generation of cytotoxic T cells is normally favoured by a so-called Th1 response, in which antigen is presented in the context of MHC class I molecules. The predominant cytokines produced in Th1 responses are interferon gamma, IL-2, TNF alpha and beta and GM-CSF. Serum antibody may also be generated in such responses, but are likely to include IgG2a, rather than IgG1.

Th2 responses may be favoured by soluble antigen which may be taken up by antigen presenting cells. Th1 responses may be favoured by cytosolic production of antigen, which facilitates presentation via MHC class I molecules. See, for example, Rush et al. (2002) J. Immunol. 169: 4951-4960.

Modes of Administration, and Pharmaceutical Formulations

The proteins described in this specification may be administered directly to subjects.

Alternatively, a nucleic acid encoding the fusion protein may be administered to a subject such that the fusion protein is expressed from the subject's own cells. Typically the nucleic acids will be part of one or more expression vectors, which may be administered as naked nucleic acid or in a delivery vehicle such as a viral vector (e.g. a retroviral, lentiviral or adenoviral vector). The vector could be targeted to selected cell types for production of the fusion proteins, or it could contain regulatory elements which are switched on more or less selectively in those selected cell types.

The expression vector will contain an open reading frame encoding the fusion protein, optionally containing one or more introns, operably linked to appropriate regulatory sequences to drive expression of the fusion protein in one or more types of eukaryotic (particularly mammalian) cell. Regulatory sequences including promoter sequences, enhancer sequences, and transcriptional and translational terminator sequences. the vectors may contain one or more marker genes and other sequences as appropriate. The skilled person will be capable of designing a suitable vector for expression of the fusion protein.

The fusion protein is typically secreted from the cell expressing it. The open reading frame encoding the fusion protein may therefore contain a suitable signal sequence capable of directing the fusion protein into the secretory pathway of the appropriate mammalian cell type. Suitable signal sequences are well-known to the skilled person. The signal sequence will typically be derived from a mammalian gene, or from a gene from a virus capable of infecting mammalian cells. Preferably it is derived from a gene from the same species as the cell in which the fusion protein is to be expressed.

Cells capable of expressing and secreting the fusion protein may also be administered to the subject. Thus a cell may be administered which contains a nucleic acid or expression vector as described above. These cells may be syngeneic or histocompatible with the subject; for example, they may have been obtained from the subject, engineered to express the fusion protein, and readministered to the subject (optionally after one or more divisions in culture in order to increase the cell number). Alternatively they may be xenogeneic (derived from a different species to the subject) or allogeneic (derived from a different member of the same species as the subject), in which case they may be treated to prevent or reduce rejection by the subject's immune system. For example, they may be encapsulated in an inert polymer.

All such proteins, nucleic acids and cells will typically be administered as part of a pharmaceutical composition. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration.

Administration may be via any suitable route. Mucosal administration may be desirable if it is intended to generate a mucosal immune response, so that the fusion protein is absorbed through a mucosal surface. Mucosal routes include nasal, buccal, rectal, vaginal or oral (for uptake through the intestinal mucosa). For generating systemic immune response, the route of administration may be less important and may include oral administration or any suitable parenteral route including intravenous, cutaneous or subcutaneous, nasal, intramuscular and intraperitoneal routes.

Nucleic acids are typically administered transdermally, but other routes, including mucosal administration, are possible.

Pharmaceutical compositions for oral administration may be in tablet, capsule, powder or liquid form. A tablet may include a solid carrier such as gelatin. Liquid pharmaceutical compositions generally include a liquid carrier such as water, petroleum, animal or Vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The compositions described here may be administered in conjunction with one or more other adjuvants in order to increase the immunogenicity of the peptide antigen yet further.

Whatever the nature of the active agent that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in *Remington's Pharmaceutical Sciences,* 20th Edition, 2000, pub. Lippincott, Williams & Wilkins.

A composition may be administered alone or in combination with other treatments, either simultaneously or sequentially dependent upon the condition to be treated.

A notable characteristic of the fusion proteins described in this specification is that, unusually, just one administration can lead to a detectable immune response against the peptide antigen. Nevertheless, to optimise the response obtained, it may be desirable to administer more than one dose, the doses being separated by suitable intervals of time, e.g. at least a week, at least two weeks, or at least one month.

EXAMPLES

Materials and Methods
Construction of Expression Vectors
pET33b-eGFPPLY

Figure 1:
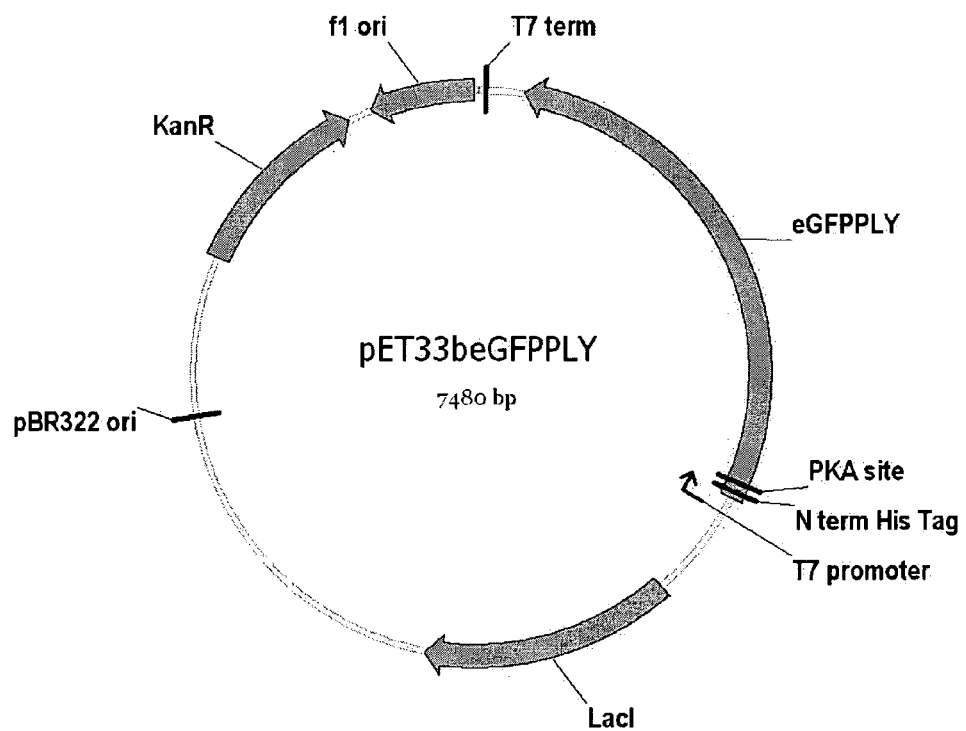
FIG. 1: Plasmid map of eGFPPLY construct.

The GFP coding sequence was amplified from pNF320 [15] by PCR using primers 20G and 20H (see Table 1). The amplified product was digested with NheI and BglII, ligated into NheI/BamHI-digested pET33bPLY and transformed into TOP10 E. coli (Invitrogen). FIG. 1a shows the map of the plasmid constructed. Mutations F64L and S65T [16] were introduced into GFP by site-directed mutagenesis (Quikchange SDM Kit, Stratagene) using primers 24W and 24X.

pET33b-Del6eGFPPLY

Δ6eGFPPLY was constructed by site-directed mutagenesis (Quikchange SDM Kit, Stratagene) of pET33b-eGFPPLY using primers 23B and 23C to introduce the Δ6 mutation (Deletion of A146 and R147) within the ply coding sequence.

pET33b-eGFP

The coding sequence for eGFP was amplified by PCR from pET33b-eGFPPLY using primers 20G and 45L (see Table 1). The resulting product was cut with NheI and SacI, gel purified and ligated into NheI/SacI cut, CIAP-treated pET33b. The ligation reaction was transformed into XL-1 cells (Stratagene)

Vector Encoding PsaAPly Fusion Protein

To create a destination vector suitable for use in the Gateway® Cloning LR (Invitrogen) reaction, a Gateway® reading frame cassette was ligated into blunt ended, CIAP-treated pET33bPly and transformed into DB3.1 E. coli cells which are resistant to the effects of the ccdB death gene found in the Gateway® cassette. This plasmid was designated pET33bGatewayPly.

Genomic fragments corresponding to the most immunogenic portion of pneumococcal surface adhesin A (PsaA) were amplified by PCR and cloned into the pET33bGatewayPly vector in a two step Gateway® cloning reaction.

Primers (Sigma-Genosys Ltd., Haverhill, United Kingdom) were designed to amplify a 867 by region of psaA from D39 S. pneumoniae genomic DNA using PCR. Nucleotides corresponding to amino acids 1 to 290 of the mature PsaA polypeptide were amplified using primers shown below. The first 30 nucleotides coded for the attB fragment and the remaining nucleotides were sequence specific. Primers were ordered in a desalted, dry format and resuspended in TE buffer to a 100 μM concentration.

Recombination of the PCR product with the pDONR™/Zeo vector in a BP reaction led to the creation of entry clones, which were transformed into DH5α E. coli. Entry clones positive for the presence of the psaA gene were recombined in a LR reaction with pET33bGatewayPly destination vector to create expression clones. These were transformed into DH5α E. coli. Successful transformants were propagated and used for the expression of PsaAPly protein.

TABLE 1

Primers used in amplification.
The nucleotide sequences provided are
SEQ ID NOs: 16-24, from top to bottom.

| Primer Ref | Primer Name | Sequence (5' to 3') |
|---|---|---|
| 20G | GFPpET33bFwd | GTCAGGCTAGCATGAGTAAAGGAGAAG AAC |
| 20H | GFPpET33brev | CCACGCAGATCTTTGTATAGTTCATCC |
| 23B | PLY LKΔ6fwd | GGTCAATAATGTCCCAATGCAGTATGA AAAAATACGGCTC |
| 23C | PLY LKΔ6rev | GAGCCGTTATTTTTCATACTGCATTG GGACATTATTGACC |
| 24W | GFP-S65T-F64L-Fwd | CACTTGTCACTACTCGACTTATGGTGT TCAATGC |
| 24X | GFP-S65T-F64L-Rev | GCATTGAACACCATAAGTCAGAGTAGT GACAAGTG |
| 45L | GFPpET33bTermRev | CCACGCGAGCTCTTATTTGTATAGTTC ATCC |
| 48E | PsaA-frag Gateway fwd | GGGGACAAGTTTGTACAAAAAAGCAGG CTTCGCTAGCGGAAAAAAGAT |
| 48F | PsaA-frag Gateway rev | GGGGACCACTTTGTACCCGAAAGCTGG GTCTTTTGCCAATCCTTCAGC |

All plasmids were transformed into BL21(DE3) E. coli for protein expression, except for the PsaPly construct which was transformed into DH5α E. coli.

The construction of all plasmids was checked by DNA sequencing by the Molecular Biology Support Unit, University of Glasgow.

Protein Expression and Purification

Recombinant E. coli containing either pET33beGFPPLY or pET33b-Del6eGFPPLY were grown in terrific broth containing kanamycin with shaking at 37° C. until they had reached an $OD_{600}$ of 1Unit. Expression of the recombinant protein was then induced by addition of 1 mM IPTG and the bacteria grown for a further 3 h before bacterial cells were harvested by centrifugation. Bacterial pellets were disrupted by sonication and the cell lysates were centrifuged at 18000 g for 30 minutes to remove cell debris.

E. coli containing the pET33beGFP plasmid were prepared as described above except that following induction, bacteria were left to grow overnight before harvesting the cells by centrifugation.

PsaAPly was expressed in BL21 (RIPL) cells from Stratagene that were grown in Terrific Broth until an O.D. of 0.6 was reached. The cells were then induced with isopropyl-beta-D-thiogalactopyranoside (IPTG) at 1 mM concentration for 2 hours. The cells were pelleted and resuspended in PBS before being disrupted using a Constant Flow Cell Disruptor at 20000 psi. The lysate was clarified by centrifugation at 13000 rpm for 30 min and filtered using 0.22 μm syringe filters.

Purification of Egfpply by Hydrophobic Interaction Chromatography eGFPPLY and Del6eGFPPLY were purified from cell supernatants by hydrophobic interaction chromatography using a PE matrix on a BioCad 700E workstation (PerSeptive Biosystems). Purified proteins were dialysed into 0.1M phosphate buffer and further purified by anion exchange (HQ) chromatography was performed using the BioCad. Following elution with 150 mM NaCl, the proteins were immediately dialysed against PBS and concentrated using Amicon Ultra centrifugal concentrators (Millipore) with 30 kDa cut-off membranes.

Nickel-Affinity Chromatography eGFP was purified by FPLC on a Nickel-charged NTA Superflow (Qiagen) column, with elution on a 0-300 mM continuous imidazole gradient in PBS. Purified proteins were dialysed three times against a greater than 50-fold volume of PBS and concentrated using Amicon Ultra centrifugal concentrators (Millipore) with a minimal 10 kDa range.

Purification of PsaAPly and Ply

PsaAPly was purified using metal affinity chromatography (MAC), size exchange chromatography (SEC) and anion exchange chromatography (AEC) PsaA was purified from a pQE31 expression vector in BL21 (DE3) *E. coli* in Luria Broth using MAC and AEC. All proteins were checked for purity using SDS-PAGE and Coomassie Blue staining.

Analysis of the Proteins.

Concentration

Total protein measurements of the proteins were calculated using a standard Bradford assay. The concentration of eGF-PPLY, De16eGFPPLY and eGFP was 0.63 mg/ml, 0.7 mg/ml and 3.84 mg/ml respectively. The proteins were also further analysed for presence of other contaminating proteins or degeneration of the protein using overloaded SDS/PAGE or western blots respectively.

LPS Levels

Following purification, both antigens were tested for the presence of contaminating Gram negative LPS using a colorimetric LAL assay (KQCL-BioWhittaker). This assay indicated that there was less that 5IU/of LPS per immunisation dose, a level that is currently acceptable in manufactured vaccines for human health. This level is also considered insufficient for the LPS to activate immunological responses non-specifically.

Haemolytic Activity

Haemolytic assays were performed by a modification of technique described by Walker et al 1987 [17]. In brief, horse defibrinated blood was exposed to decreasing concentrations of the eGFPPLY, De16eGFPPLY or eGFP proteins in round bottomed 96 well plates. Following incubation, the plates were centrifuged at 1000 G and 50 µl supernatant from each well was transferred to a new plate. The absorbance at 540 nM was measured using a 96 well plate reader and the $A_{540}$ for each sample was expressed as a percentage of the $A_{540}$ for a completely lysed control well Animals and Immunisation Groups of five female BALB/c mice aged 6-8 weeks (Harlan Olac, UK) were immunised intranasally (i.n.) with either the toxin admixed with the eGFP protein or given as a genetically fused conjugated protein (as described in table 2). To reduce the impact of toxicity, animals were immunised with increasing doses of antigen. For the first immunisation 0.2 ug of PLY was admixed with approx 0.1 ug of eGFP. This was calculated to ensure the ratio of PLY to eGFP was identical to that present in an equivalent dose of the eGFPPLY protein. Similar concentrations of LT (0.2 ug) and eGFP (0.1 ug) were administered to those animals receiving LT+eGFP or eGFP alone. For subsequent immunisations, doses equivalent to 0.4 and 0.8 of PLY were administered.

In the second experiment, eGFPPLY was administered at the same concentration as described above for the first three immunisations, however a fourth 0.8 ug dose was also given. In this experiment, the concentration of De16eGFPPLY and LT were increased tenfold resulting in concentrations of 2, 4, 8, 8 ug of toxins given in each subsequent dose. For the LT group approximately 1, 2, 4 and 4 ug of eGFP were admixed with the toxin. Animals given eGFP alone were immunised using the higher concentration of eGFP administered with LT. Each dose was diluted to a final volume of 20 ul in PBS (pH7.2) and 10 ul was administered to the nostrils of lightly anaesthetised animals. Mice were immunised on days 1, 14, 28 and 42. Serum samples were collected from the tail vein of each animal 1 day prior to immunisation, day 13, day 27 and day 41. All animals were exsanguinated on day 42 (expt 1) or day 56 (expt 2) by cardiac puncture. Nasal and lung lavages were performed on day 42 or 56 respectively using 0.1% (wt/vol) bovine serum albumin in PBS. Samples were all stored frozen prior to testing.

In the third experiment, Female Balb/c and MF1 mice aged 6-8 weeks old were obtained from Harlan, Bichester, United Kingdom. Mice were lightly anesthetized with 2% halothane-1.5% oxygen (1.5 liter/min) (Astra-Zeneca, Macclesfield, United Kingdom) and treated intranasally (i.n.) with purified EGFPPly, PsaAPly or PsaA at 0.1 µg toxin/dose in 25 µl of saline with a saline-only control group (n=4 to 8). PsaA concentration was adjusted to be the same molar quantity as that in the fusion protein. Subsequent boosts used 0.2 and 0.4 µg toxin/dose respectively on days 22 and 35/40. Blood was taken from the lateral tail vein prior to each dose. Mice were culled on day 77 and nasal and lung lavage was performed (n=4).

Challenge with *S. pneumoniae*

Mice that had received the previous vaccination schedule were heavily anaesthetized with 2% halothane-1.5% oxygen (1.5 liter/min) (Astra-Zeneca, Macclesfield, United Kingdom). They were then inoculated i.n. with either $10^5$ or $10^6$ colony forming units of TIGR4 *S. pneumoniae* in 50 µl PBS at least 4 weeks after the last boost. Mice were weighed and monitored for pain before they were culled at 48 hours and processed for bacterial counts in the nasal tissue and nose wash, bronchoalveolar lavage fluid and lung tissue, and blood (n=8). Pain scores were attributed according to a scale that uses morbidity rather than mortality as an end point. This scale is detailed below:

| Condition | Level | Description | Overall pain score |
|---|---|---|---|
| Normal | | Normal stance and movement | 0 |
| Hunched | 1 | Slightly hunched stance | 1 |
| | 2 | Pronounced hunched stance | 2 |
| Starey coat | 1 | Mild piloerection of coat, mainly around the back of the neck | 3 |
| | 2 | Marked piloerection over whole body | 4 |
| Lethargic | 1 | Slightly slower movement than usual | 5 |
| | 2 | Obviously slower movement than usual | 6 |
| Moribund | | Unwillingness to move when encouraged to do so | 7 |

ELISA

Anti-PLY and anti eGFP responses within individual serum samples were determined by enzyme linked immunosorbant assay (ELISA). These assays were performed as described (1) with ELISA plates coated overnight at 4° C. with eGFP (0.1 ug/well in PBS) or PLY (0.02 ug/well in PBS). ELISA titres were calculated as the reciprocal of the of the highest serum dilution which gave an absorbance of 0.3 above the background.

The levels of anti-PLY and eGFP within the mucosal lavage samples were determined by ELISA as described above except biotinylated IgA (Sigma) was used as the detection antibody. ELISA titres were calculated as the reciprocal of the highest dilution that gave an absorbance of 0.2 above the background.

Results

Haemolytic Activity

Figure 2:
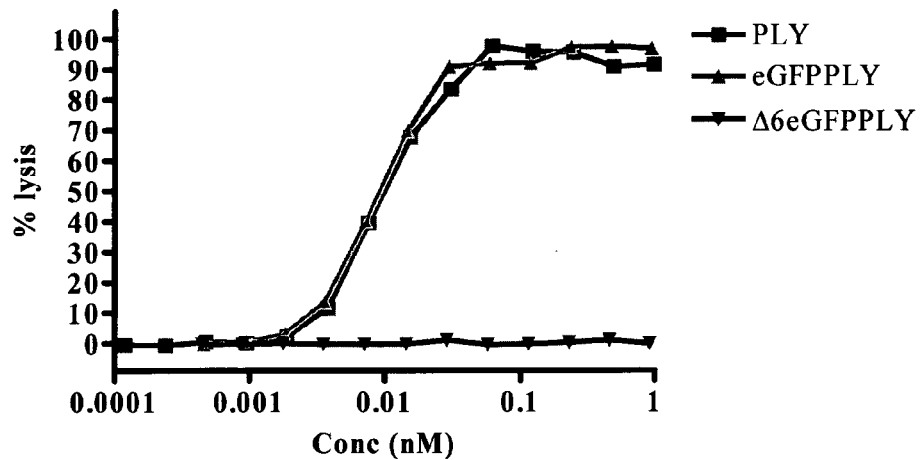
FIG. 2: Haemolytic activity of the various derivatives of PLY to red blood cells.

The haemolytic activity of the proteins was tested in a standard haemolytic assay. The results shown in FIG. 2 indicate that conjugation of the eGFP protein to the native form of PLY does not affect the haemolytic activity of the protein. As expected the Del6eGFPPLY protein has no detectable haemolytic activity.

In vivo Testing—Experiment 1

The aim of this experiment was to determine whether PLY could act as a mucosal adjuvant to eGFP when administered intranasally to mice as genetically fused proteins or as unlinked proteins.

In this first experiment, animals were immunised with increasing doses of eGFP and PLY as a simple admixed formulation or as the genetic fusion protein eGFPPLY. In this experiment, LT, which is a well-described mucosal adjuvant acted as a positive control. In addition the non-toxic version of PLY (Del6PLY) was formulated and delivered admixed with eGFP or given as a genetic fusion protein (Del6eGFPPLY)

Figure 3:
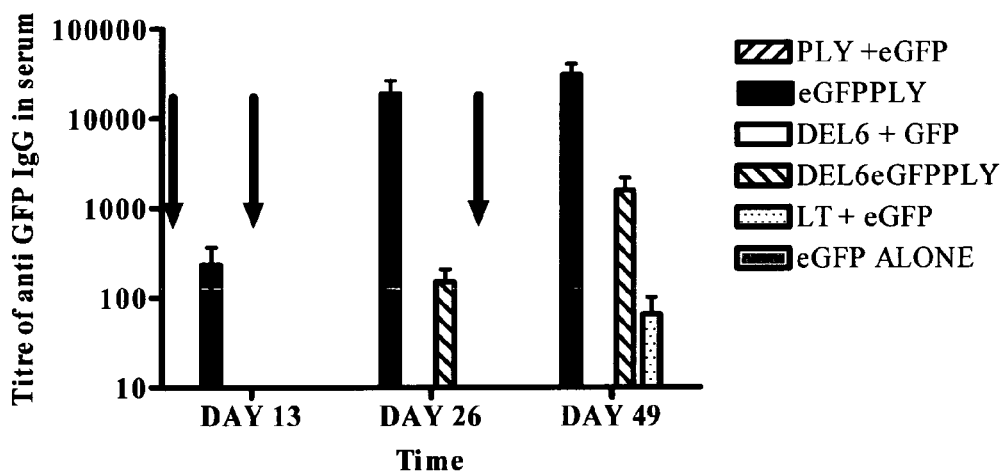
FIG. 3: Immune responses to eGFP in the serum of mice immunised with different vaccination combinations. Each bar represents the geometric mean titre for 5 mice per group and each error bar the standard deviation from the mean. Arrows indicate times of vaccination.

From data presented in FIG. 3, it would appear that administration of the eGFPPLY resulted in the production of high levels of antibodies to eGFP. In contrast, no response was observed when PLY and eGFP admixed formulation was given. These data are particularly interesting as unlike other previously described adjuvants such as LT, the response to the conjugated antigen was rapid being detectable following a single immunisation. In addition, the concentration of antigen required to stimulate this response was low, with responses being generated using five fold lower amounts of eGFPPLY than is usually described for LT. In fact the relative poor response demonstrated by LT in this experiment probably reflects the fact that LT was given at a relatively low dose to allow direct comparison with the eGFPPLY fusion protein.

Figure 4A:
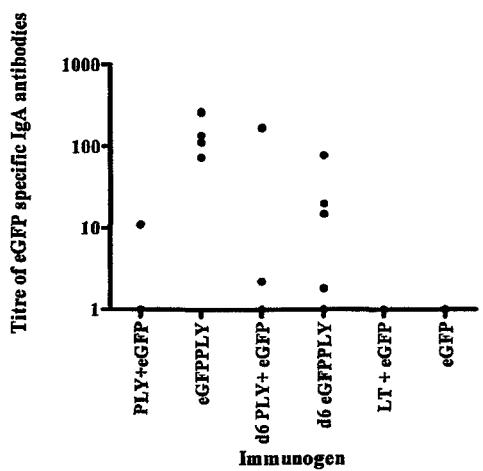
FIG. 4A-FIG. 4B: Titre of eGFP specific IgA detected in the mucosal washes of the nose (FIG. 4A) and lungs (FIG. 4B) of immunised animals. Each dot represents an individual animal (5 animals per group) and each line the mean response of the 5 individual animals
Figure 4B:
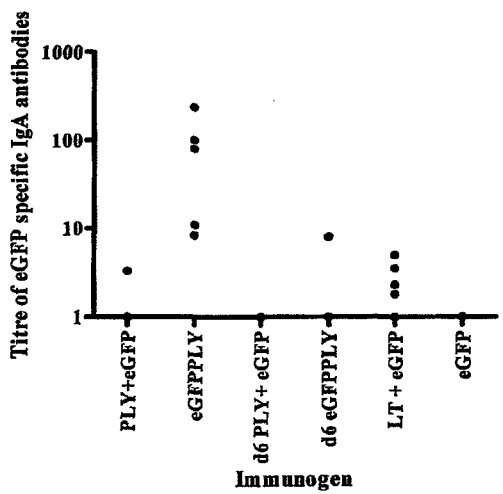

Mucosal responses to the antigens were also tested and the results (shown in FIG. 4) clearly show that mucosal IgA to eGFP were generated in all animals immunised with the eGFPPLY fusion and that these were present in both the nasal (nasal wash—FIG. 4a) and pulmonary tract (lung wash—FIG. 4b). In contrast, no eGFP IgA was observed in animals given either eGFP alone or that admixed with the PLY protein. Small responses to eGFP were observed in those animals given LT as an adjuvant but these were only detected in the lung washes of immunised animals.

Figure 5:
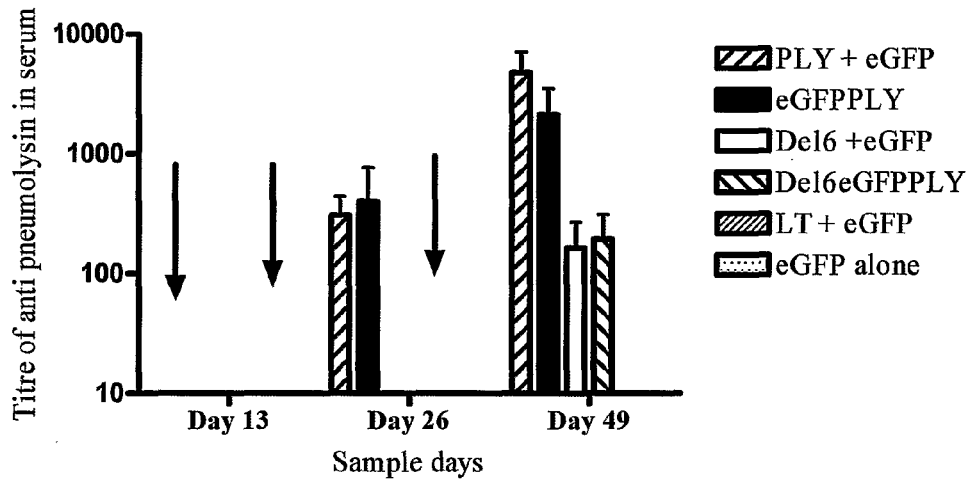
FIG. 5: Immune responses to pneumolysin in the serum of animals over time. Each bar represents the geometric mean titre for 5 mice per group and each error bar the standard deviation from the mean. Arrows indicate times of vaccination.

Together these results suggest that PLY is able to efficiently deliver fused antigens to the mucosal surface of the respiratory tract, resulting in the rapid production of antibodies to that antigen both in the blood and on the mucosal surface, Anti-Pneumolysin Responses In contrast to the GFP responses, the immune response to pneumolysin itself was limited. No response was observed after a single dose of the toxin (FIG. 5) and low but detectable responses for Del6eGFPPLY were only observed after 3 doses of the toxin were given. Mucosal responses were only observed in only 1 animal per group of five immunised with the PLY alone or as a conjugate protein. This is useful if this protein is to be used as a basis for multivalent vaccines.

In vivo testing—Experiment 2

The aim of this experiment was to determine the reproducibility of the adjuvant activity for the eGFP construct and to compare data with that generated using previously published concentrations of LT.

In this experiment, mice were immunised either with eGFPPLY at the concentrations as used for the first experiment or 10 fold higher concentrations for both Del6eGFPPLY and LT (LT first dose 2 ug of LT admixed with 1 ug of eGFP). The eGFP given as a control was administered at the higher concentration.

Figure 6:
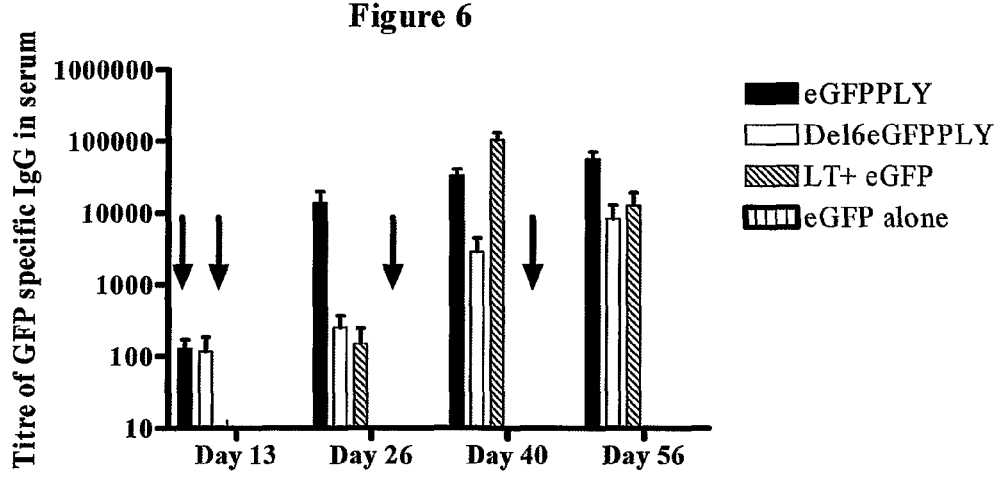
FIG. 6: Immune responses to eGFP in the serum of animals over time. Each bar represents the geometric mean titre for 5 mice per group and each error bar the standard deviation from the mean. Arrows indicate times of vaccination.

Results shown in FIG. 6 indicate that as for the first experiment, anti eGFP responses were detectable in the serum of animals after a single intranasal administration of the eGFPPLY conjugate. These responses were enhanced on boosting. In contrast no serum responses were detected in any of the animals immunised with eGFP. In contrast to the first experiment and in agreement with the literature, responses to eGFP were detected in the serum of animals given eGFP and LT. This probably reflects the higher dose of LT given in this experiment. Although a fourth dose was given in this experiment, it does not appear to be required as data from the serum would suggest the maximum response to the antigen has been achieved. In this experiment the non-toxic Del6eGFPPLY is as effective, as the highly toxic LT at inducing immune responses to the eGFP protein.

Figure 7:
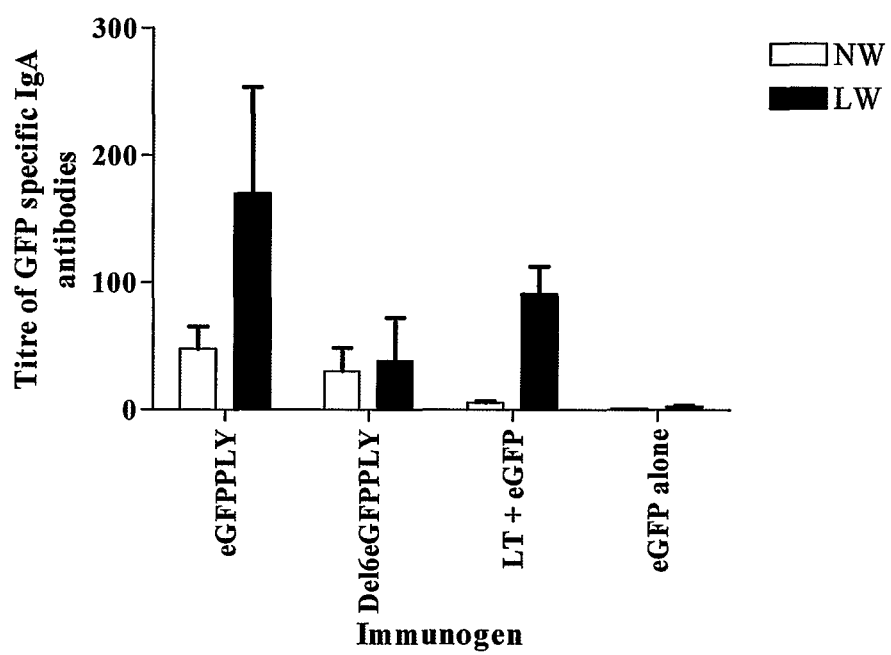
FIG. 7: Mean titres of eGFP specific IgA in the nasal and lung lavages of animals immunised intranasally with eGFP-PLY, LT+eGFP or eGFP alone. The results show the calculated geometric mean titre of IgA in the nasal wash (□) or lung wash (■) from 5 animals per group. The error bars reflect the standard deviation from the mean of each group.

Mucosal responses to eGFP also confirmed previous observations with high levels of eGFP IgA present in both the nasal and pulmonary tracts of animals immunised with the eGFP-PLY fusion (FIG. 7). Interestingly, as reported previously, LT appears to generate higher levels of antigen specific IgA in the lungs, with less detected in the nasal samples. In contrast, in the two experiments performed using eGFPPLY the levels of eGFP specific IgA in the lungs and nasal tissue have not reflected any level of bias, in fact antigen specific IgA appears to be equally stimulated at the two locations. This may reflect differences in the specific ligand used by these toxins when interacting with the host cells. The low level of eGFP specific IgA detected in this experiment in the eGFP control group probably reflects the impact of multiple vaccinations with a relative high concentration of eGFP.

In vivo testing—Experiment 3

The aim of this experiment was to test the ability of a PsaA-Ply fusion protein to induce a protective immune response against *S. pneumoniae*.

PsaA (Pneumococcal surface antigen A) is known to be capable of inducing a protective immune response against *S. pneumoniae*. Animals were vaccinated intranasally with a PsaA-Ply fusion protein, or with eGFPLY, PsaA alone, or PBS vehicle control. At least 4 weeks after the final boost, they were challenged intra-nasally with live *S. pneumoniae*. Pain scores (as an indication of symptoms of bacterial infection) were determined at 0, 24 and 48 hours (FIG. 9), and bacterial load in blood at 24 and 48 hours (FIG. 10). Bacterial loads in the respiratory tract at 48 hours were also determined (data not shown). Results with the PsaAPly fusion protein are clearly superior to those achieved with PsaA alone.

CONCLUSION

Pneumolysin generated by *Streptococcus pneumoniae* is described as a pore forming cytolysin. However, to describe its activity in terms of its pore forming activity hugely understates its ability to modulate the immune response to both itself and to the organism from which it is generated.

In these experiments we have shown how this immunomodulatory capacity can be harnessed to generate the type of rapid and specific immune response that are essentials characteristics of new vaccine formulations. Intranasal vaccination with the model antigen eGFP fused to PLY resulted in seroconversion of all animals after a single dose of a relatively small amount of fusion protein (less than 0.2 ug of PLY). This response was boostable on further exposure to the toxin and generated detectable antigen specific IgA responses to eGFP in mucosal secretions. These responses equivalent to those generated by administration of eGFP with native LT (the previously most effective mucosal adjuvant tested) however, significantly higher levels of LT are required to generate such a response.

In these experiments activity has been demonstrated using the model antigen (eGFP), and we believe that this principle could be applied to any antigen, including but not limited to those from viral, bacterial and other parasitic pathogens. These could be fused to the PLY for potentially successful delivery to the immune system. This provides the potential for the development of a generic vaccine platform to which many different antigens could be rapidly applied. One advantage of this approach would appear to be the relatively low response generated to the PLY itself. In contrast to LT, in which strong responses are first generated to the toxin, in these experiments, it would appear that anti-PLY responses are low.

REFERENCES

1. Douce, G., M. M. Giuliani, V. Giannelli, M. G. Pizza, R. Rappuoli, and G. Dougan, *Mucosal immunogenicity of genetically detoxified derivatives of heat labile toxin from Escherichia coli. Vaccine,* 1998. 16(11-12): p. 1065-1073.
2. Elson, C. O. and W. Ealding, *Generalized systemic and mucosal immunity in mice after mucosal stimulation with cholera toxin*. J Immunol, 1984. 132(6): p. 2736-41.
3. Clements, J. D., N. M. Hartzog, and F. L. Lyon, *Adjuvant activity of Escherichia coli heat-labile enterotoxin and effect on the induction of oral tolerance in mice to unrelated protein antigens*. Vaccine, 1988. 6(3): p. 269-77.
4. Douce, G., C. Turcotte, I. Cropley, M. Roberts, M. Pizza, M. Domenghini, R. Rappuoli, and G. Dougan, *Mutants of Escherichia-Coli Heat-Labile Toxin Lacking Adp-Ribosyltransferase Activity Act As Nontoxic, Mucosal Adjuvants*. Proceedings of the National Academy of Sciences of the United States of America, 1995. 92(5): p. 1644-1648.
5. Dickinson, B. L. and J. D. Clements, *Dissociation of Escherichia coli heat-labile enterotoxin adjuvanticity from ADP-ribosyltransferase activity*. Infect Immun, 1995. 63(5): p. 1617-23.
6. Yamamoto, S., H. Kiyono, M. Yamamoto, K. Imaoka, K. Fujihashi, F. W. Van Ginkel, M. Noda, Y. Takeda, and J. R. McGhee, *A nontoxic mutant of cholera toxin elicits Th2-type responses for enhanced mucosal immunity*. Proc Natl Acad Sci U S A, 1997. 94(10): p. 5267-72.
7. Komase, K., S. Tamura, K. Matsuo, K. Watanabe, N. Hattori, A. Odaka, Y. Suzuki, T. Kurata, and C. Aizawa, *Mutants of Escherichia coli heat-labile enterotoxin as an adjuvant for nasal influenza vaccine*. Vaccine, 1998. 16(2-3): p, 248-54.
8. Giuliani, M. M., G. Del Giudice, V. Giannelli, G. Dougan, G. Douce, R. Rappuoli, and M. Pizza, *Mucosal adjuvanticity and immunogenicity of LTR72, a novel mutant of Escherichia coli heat-labile enterotoxin with partial knockout of ADP-ribosyltransferase activity*. J Exp Med, 1998. 187(7): p. 1123-32.
9. Rubins, J. B., D. Charboneau, C. Fasching, A. M. Berry, J. C. Paton, J. E. Alexander, P. W. Andrew, T. J. Mitchell, and E. N. Janoff, *Distinct role for pneumolysin's cytotoxic and complement activities in the pathogenesis of pneumococcal pneumonia*. Am. J. Respir. and Critical Care Medicine, 1996. 153: p. 1339-1346.
10. Hirst, R. A., K. S. Sikand, A. Rutman, T. J. Mitchell, P. W. Andrew, and C. Ocallaghan, *Relative roles of pneumolysin and hydrogen peroxide from Streptococcus pneumoniae in inhibition of ependymal ciliary beat frequency*. Infection and Immunity, 2000. 68(3): p. 1557-1562.
11. Braun, J. S., J. E. Sublett, D. Freyer, T. J. Mitchell, J. L. Cleveland, E. I. Tuomanen, and J. R. Weber, *Pneumococcal pneumolysin and H2O2 mediate brain cell apoptosis during meningitis*. Journal of Clinical Investigation, 2002. 109(1): p. 19-27.
12. Stringaris, A. K., J. Geisenhainer, F. Bergmann, C. Balshusemann, U. Lee, G. Zysk, T. J. Mitchell, B. U. Keller, U. Kuhnt, J. Gerber, A. Spreer, M. Bahr, U. Michel, and R. Nau, *Neurotoxicity of Pneumolysin, a Major Pneumococcal Virulence Factor, Involves Calcium Influx and Depends on Activation of p38 Mitogen-Activated Protein Kinase*. Neurobiol Dis, 2002. 11(3): p. 355-68.
13. Malley, R., P. Henneke, S. C. Morse, M. J. Cieslewicz, M. Lipsitch, C. M. Thompson, E. Kurt-Jones, J. C. Paton, M. R. Wessels, and D. T. Golenbock, *Recognition of pneumolysin by Toll-like receptor 4 confers resistance to pneumococcal infection*. PNAS, 2003: p. 0435928100.
14. Singh, R., M. E. Dominiecki, E. M. Jaffee, and Y. Paterson, *Fusion to Listeriolysin O and Delivery by Listeria monocytogenes Enhances the Immunogenicity of HER-2/neu and Reveals Subdominant Epitopes in the FVB/N Mouse*. J Immunol, 2005. 175(6): p. 3663-3673.
15. Freitag, N. E. and K. E. Jacobs, *Examination of Listeria monocytogenes intracellular gene expression by using the green fluorescent protein of Aequorea victoria*. Infect Immun, 1999. 67(4): p. 1844-52.
16. Cormack, B. P., R. H. Valdivia, and S. Falkow, *FACS-optimized mutants of the green fluorescent protein* (GFP). p. 33-8.
17. Walker, J. A., R. L. Allen, P. Falmagne, M. K. Johnson, and G. J. Boulnois, *Molecular cloning, charcaterization, and complete nucleotide sequence of the gene for pneumolysin, the sulfhydryl-activated toxin of Streptococcus pneumoniae*. Infect. Immun., 1987. 55: p. 1184-1189.

The invention claimed is:

1. A method of generating a mucosal immune response against a peptide antigen, comprising administering to a subject a protein comprising a single chain of amino acids forming a fusion protein of said peptide antigen and a cytolysin, wherein said cytolysin is selected from the group consisting of pneumolysin from *Streptococcus pneumoniae*, perf

*Streptococcus intermedius*, alveolysin from *Bacillus alvei*, anthrolysin from *Bacillus anthracis*, putative cereolysin from *Bacillus cereus*, ivanolysin O from *Listeria ivanovii*, pyolysin from *Arcanobacterium pyogenes*, suilysin from *Streptococcus suis*, tetanolysin from *Clostridium tetani*, thuringiolysin O from *Bacillus thuringiensis*, botulinolysin from *Clostridium botulinum*, chauveolysin from *C. chauvoei*, bifermentolysin from *C. bifermentans*, sordellilysin from *C. sordellii*, histolyticolysin from *Clostridium histiolyticum*, novylysin from *Clostridium novyi* and septicolysin O from *Clostridium septicum*, and wherein said peptide antigen is derived from an infectious organism.

2. The method according to claim 1, wherein said mucosal immune response includes at least one of increased IgA production and activation of lymphocytes in mucosal-associated lymphoid tissue, wherein the immune response is generated for prophylaxis or therapy of infection by the infectious organism.

3. The method according to claim 2 wherein the peptide antigen is derived from the same organism as the cytolysin.

4. The method according to claim 1 wherein the peptide antigen is derived from a different organism to the cytolysin.

5. The method according to claim 4 wherein the peptide antigen is derived from an organism which does not express a cytolysin.

6. The method according to claim 1 wherein the fusion protein is used to generate or enhance generation of serum antibodies against the peptide antigen, or against the protein from which the peptide antigen is derived.

7. The method according to claim 6 wherein administration is selected from the group consisting of oral, intravenous, intramuscular, intraperitoneal, cutaneous, subcutaneous, transdermal and mucosal administration.

8. The method according to claim 1 wherein administration is mucosal.

9. The method according to claim 8 wherein administration is nasal.

10. The method according to claim 1 wherein the cytolysin is a mutant comprising a mutation which affects a biological activity of the cytolysin selected from the group consisting of haemolytic activity, ability to oligomerise, and ability to activate complement.

11. The method according to claim 10 wherein the cytolysin is a mutant comprising a deletion of at least one amino acid within the region corresponding to amino acids 144 to 151 of a wild type pneumolysin sequence.

12. The method according to claim 2, wherein the infectious organism is an intracellular or extracellular bacteria, a virus, a fungus, or a parasite.

13. The method according to claim 12, wherein the parasite is a malaria parasite.

* * * * *

SEQUENCE LISTING

```
<160> NUMBER OF SEQ ID NOS: 38

<210> SEQ ID NO 1
<211> LENGTH: 18
<212> TYPE: PRT
<213> ORGANISM: Artificial Sequence
<220> FEATURE:
<223> OTHER INFORMATION: Synthetic sequence

<400> SEQUENCE: 1
```

Val Pro Ala Arg Met Gln Tyr Glu Lys Ile Thr Ala His Ser Met Glu
1               5                   10                  15

Gln Leu

<210> SEQ ID NO 2
<211> LENGTH: 18
<212> TYPE: PRT
<213> ORGANISM: Artificial Sequence
<220> FEATURE:
<223> OTHER INFORMATION: Synthetic sequence

<400> SEQUENCE: 2

Leu Pro Ala Arg Thr Gln Tyr Ser Glu Ser Met Val Tyr Ser Lys Ser
1               5                   10                  15

Gln Ile

<210> SEQ ID NO 3
<211> LENGTH: 18
<212> TYPE: PRT
<213> ORGANISM: Artificial Sequence
<220> FEATURE:
<223> OTHER INFORMATION: Synthetic sequence

<400> SEQUENCE: 3

Ile Asn Ala Lys Ile Asp Tyr Ser Asp Glu Met Ala Tyr Ser Glu Ser
1               5                   10                  15

Gln Leu

<210> SEQ ID NO 4
<211> LENGTH: 18
<212> TYPE: PRT
<213> ORGANISM: Artificial Sequence
<220> FEATURE:
<223> OTHER INFORMATION: Synthetic sequence

<400> SEQUENCE: 4

Leu Pro Ala Arg Thr Gln Tyr Ser Glu Ser Met Val Tyr Ser Lys Ser
1               5                   10                  15

Gln Ile

<210> SEQ ID NO 5
<211> LENGTH: 18
<212> TYPE: PRT
<213> ORGANISM: Artificial Sequence
<220> FEATURE:
<223> OTHER INFORMATION: Synthetic sequence

<400> SEQUENCE: 5

Leu Pro Ala Arg Thr Gln Tyr Thr Glu Ser Met Val Tyr Ser Lys Ser
1               5                   10                  15

Gln Ile

<210> SEQ ID NO 6
<211> LENGTH: 18
<212> TYPE: PRT
<213> ORGANISM: Artificial Sequence
<220> FEATURE:
<223> OTHER INFORMATION: Synthetic sequence

<400> SEQUENCE: 6

Val Pro Ala Arg Met Gln Tyr Glu Ser Ile Ser Ala Gln Ser Met Ser
1               5                   10                  15

Gln Leu

<210> SEQ ID NO 7
<211> LENGTH: 18
<212> TYPE: PRT
<213> ORGANISM: Artificial Sequence
<220> FEATURE:
<223> OTHER INFORMATION: Synthetic sequence

<400> SEQUENCE: 7

Leu Pro Ala Arg Leu Gln Tyr Ala Glu Ser Met Val Tyr Ser Gln Asn
1               5                   10                  15

Gln Ile

<210> SEQ ID NO 8
<211> LENGTH: 18
<212> TYPE: PRT
<213> ORGANISM: Artificial Sequence
<220> FEATURE:
<223> OTHER INFORMATION: Synthetic sequence

<400> SEQUENCE: 8

Leu Pro Ala Arg Thr Gln Tyr Ser Glu Ser Met Val Tyr Ser Lys Ser
1               5                   10                  15

Gln Leu

<210> SEQ ID NO 9
<211> LENGTH: 18
<212> TYPE: PRT
<213> ORGANISM: Artificial Sequence
<220> FEATURE:
<223> OTHER INFORMATION: Synthetic sequence

<400> SEQUENCE: 9

Leu Pro Ala Arg Thr Gln Tyr Ser Glu Ser Met Val Tyr Ser Lys Ser
1               5                   10                  15

Gln Ile

<210> SEQ ID NO 10
<211> LENGTH: 18
<212> TYPE: PRT
<213> ORGANISM: Artificial Sequence
<220> FEATURE:
<223> OTHER INFORMATION: Synthetic sequence

<400> SEQUENCE: 10

Ile Ser Ala Lys Ile Asp Tyr Asp Gln Glu Met Ala Tyr Ser Glu Ser
1               5                   10                  15

Gln Leu

<210> SEQ ID NO 11
<211> LENGTH: 18
<212> TYPE: PRT
<213> ORGANISM: Artificial Sequence
<220> FEATURE:
<223> OTHER INFORMATION: Synthetic sequence

<400> SEQUENCE: 11

Thr Gln Ala Glu Leu Gln Tyr Asp Glu Thr Met Ala Tyr Ser Met Ser
1               5                   10                  15

Gln Leu

<210> SEQ ID NO 12
<211> LENGTH: 18

```
<212> TYPE: PRT
<213> ORGANISM: Artificial Sequence
<220> FEATURE:
<223> OTHER INFORMATION: Synthetic sequence

<400> SEQUENCE: 12

Ile Pro Thr Arg Met Ser Tyr Ser Asp Thr Met Val Tyr Ser Gln Ser
 1               5                  10                  15
Gln Leu

<210> SEQ ID NO 13
<211> LENGTH: 18
<212> TYPE: PRT
<213> ORGANISM: Artificial Sequence
<220> FEATURE:
<223> OTHER INFORMATION: Synthetic sequence

<400> SEQUENCE: 13

Val Ser Ala Lys Ile Asp Tyr Asp Asp Glu Met Ala Tyr Ser Glu Ser
 1               5                  10                  15
Gln Leu

<210> SEQ ID NO 14
<211> LENGTH: 18
<212> TYPE: PRT
<213> ORGANISM: Artificial Sequence
<220> FEATURE:
<223> OTHER INFORMATION: Synthetic sequence

<400> SEQUENCE: 14

Leu Pro Ala Arg Met Gln Tyr Thr Glu Ser Met Val Tyr Ser Lys Ser
 1               5                  10                  15
Gln Ile

<210> SEQ ID NO 15
<211> LENGTH: 8
<212> TYPE: PRT
<213> ORGANISM: Artificial Sequence
<220> FEATURE:
<223> OTHER INFORMATION: Synthetic sequence

<400> SEQUENCE: 15

Val Pro Ala Arg Met Gln Tyr Glu
 1               5

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
gtcaggctag catgagtaaa ggagaagaac                                    30

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
ccacgcagat ctttgtatag ttcatcc                                       27
```

<210> SEQ ID NO 18
<211> LENGTH: 41
<212> TYPE: DNA
<213> ORGANISM: Artificial Sequence
<220> FEATURE:
<223> OTHER INFORMATION: Primer

<400> SEQUENCE: 18
ggtcaataat gtcccaatgc agtatgaaaa aataacggct c                 41

<210> SEQ ID NO 19
<211> LENGTH: 41
<212> TYPE: DNA
<213> ORGANISM: Artificial Sequence
<220> FEATURE:
<223> OTHER INFORMATION: Primer

<400> SEQUENCE: 19
gagccgttat tttttcatac tgcattggga cattattgac c                 41

<210> SEQ ID NO 20
<211> LENGTH: 34
<212> TYPE: DNA
<213> ORGANISM: Artificial Sequence
<220> FEATURE:
<223> OTHER INFORMATION: Primer

<400> SEQUENCE: 20
cacttgtcac tactcgactt atggtgttca atgc                         34

<210> SEQ ID NO 21
<211> LENGTH: 35
<212> TYPE: DNA
<213> ORGANISM: Artificial Sequence
<220> FEATURE:
<223> OTHER INFORMATION: Primer

<400> SEQUENCE: 21
gcattgaaca ccataagtca gagtagtgac aagtg                        35

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
ccacgcgagc tcttatttgt atagttcatc c                            31

<210> SEQ ID NO 23
<211> LENGTH: 49
<212> TYPE: DNA
<213> ORGANISM: Artificial Sequence
<220> FEATURE:
<223> OTHER INFORMATION: Primer

<400> SEQUENCE: 23
ggggacaagt ttgtacaaaa aagcaggctt cgctagcgga aaaaaagat         49

<210> SEQ ID NO 24
<211> LENGTH: 48
<212> TYPE: DNA
<213> ORGANISM: Artificial Sequence
<220> FEATURE:
<223> OTHER INFORMATION: Primer

<400> SEQUENCE: 24 gggaccact ttgtacccga aagctgggtc ttttgccaat ccttcagc            48

<210> SEQ ID NO 25
<211> LENGTH: 471
<212> TYPE: PRT
<213> ORGANISM: Streptococcus pneumoniae

<400> SEQUENCE: 25

```
Met Ala Asn Lys Ala Val Asn Asp Phe Ile Leu Ala Met Asn Tyr Asp
  1               5                  10                  15
Lys Lys Lys Leu Leu Thr His Gln Gly Glu Ser Ile Glu Asn Arg Phe
             20                  25                  30
Ile Lys Glu Gly Asn Gln Leu Pro Asp Glu Phe Val Val Ile Glu Arg
         35                  40                  45
Lys Lys Arg Ser Leu Ser Thr Asn Thr Ser Asp Ile Ser Val Thr Ala
     50                  55                  60
Thr Asn Asp Ser Arg Leu Tyr Pro Gly Ala Leu Val Val Asp Glu
 65                  70                  75                  80
Thr Leu Leu Glu Asn Asn Pro Thr Leu Leu Ala Val Asp Arg Ala Pro
                 85                  90                  95
Met Thr Tyr Ser Ile Asp Leu Pro Gly Leu Ala Ser Ser Asp Ser Phe
            100                 105                 110
Leu Gln Val Glu Asp Pro Ser Asn Ser Ser Val Arg Gly Ala Val Asn
        115                 120                 125
Asp Leu Leu Ala Lys Trp His Gln Asp Tyr Gly Gln Val Asn Asn Val
    130                 135                 140
Pro Ala Arg Met Gln Tyr Glu Lys Ile Thr Ala His Ser Met Glu Gln
145                 150                 155                 160
Leu Lys Val Lys Phe Gly Ser Asp Phe Glu Lys Thr Gly Asn Ser Leu
                165                 170                 175
Asp Ile Asp Phe Asn Ser Val His Ser Gly Glu Lys Gln Ile Gln Ile
            180                 185                 190
Val Asn Phe Lys Gln Ile Tyr Tyr Thr Val Ser Val Asp Ala Val Lys
        195                 200                 205
Asn Pro Gly Asp Val Phe Gln Asp Thr Val Thr Val Glu Asp Leu Lys
    210                 215                 220
Gln Arg Gly Ile Ser Ala Glu Arg Pro Leu Val Tyr Ile Ser Ser Val
225                 230                 235                 240
Ala Tyr Gly Arg Gln Val Tyr Leu Lys Leu Glu Thr Thr Ser Lys Ser
                245                 250                 255
Asp Glu Val Glu Ala Ala Phe Glu Ala Leu Ile Lys Gly Val Lys Val
            260                 265                 270
Ala Pro Gln Thr Glu Trp Lys Gln Ile Leu Asp Asn Thr Glu Val Lys
        275                 280                 285
Ala Val Ile Leu Gly Gly Asp Pro Ser Ser Gly Ala Arg Val Val Thr
    290                 295                 300
Gly Lys Val Asp Met Val Glu Asp Leu Ile Gln Glu Gly Ser Arg Phe
305                 310                 315                 320
Thr Ala Asp His Pro Gly Leu Pro Ile Ser Tyr Thr Ser Phe Leu
                325                 330                 335
Arg Asp Asn Val Val Ala Thr Phe Gln Asn Ser Thr Asp Tyr Val Glu
            340                 345                 350
```

```
Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Gly Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 26
<211> LENGTH: 500
<212> TYPE: PRT
<213> ORGANISM: Clostridium perfingens

<400> SEQUENCE: 26

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
    50                  55                  60

Pro Lys Glu Gly Lys Lys Thr Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125

Ile Asn Ile Asn Ile Asp Leu Pro Gly Leu Lys Gly Glu Asn Ser Ile
    130                 135                 140

Lys Val Asp Asp Pro Thr Tyr Gly Lys Val Ser Gly Ala Ile Asp Glu
145                 150                 155                 160

Leu Val Ser Lys Trp Asn Glu Lys Tyr Ser Ser Thr His Thr Leu Pro
                165                 170                 175

Ala Arg Thr Gln Tyr Ser Glu Ser Met Val Tyr Ser Lys Ser Gln Ile
            180                 185                 190

Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
    210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255
```

```
Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
            275                 280                 285

Asp Val Gln Ala Ala Phe Lys Ala Leu Ile Lys Asn Thr Asp Ile Lys
            290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
            325                 330                 335

Asp Phe Asp Glu Ile Arg Lys Val Ile Lys Asp Asn Ala Thr Phe Ser
            340                 345                 350

Thr Lys Asn Pro Ala Tyr Pro Ile Ser Tyr Thr Ser Val Phe Leu Lys
            355                 360                 365

Asp Asn Ser Val Ala Ala Val His Asn Lys Thr Asp Tyr Ile Glu Thr
370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
            405                 410                 415

Lys Glu Gly Asn Glu Val Leu Thr His Lys Thr Trp Asp Gly Asn Tyr
            420                 425                 430

Gln Asp Lys Thr Ala His Tyr Ser Thr Val Ile Pro Leu Glu Ala Asn
            435                 440                 445

Ala Arg Asn Ile Arg Ile Lys Ala Arg Glu Cys Thr Gly Leu Ala Trp
450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
            485                 490                 495

Ile Thr Tyr Asn
            500

<210> SEQ ID NO 27
<211> LENGTH: 532
<212> TYPE: PRT
<213> ORGANISM: Streptococcus intermedius

<400> SEQUENCE: 27

Met Lys Thr Lys Gln Asn Ile Ala Arg Lys Leu Ser Arg Val Val Leu
 1               5                  10                  15

Leu Ser Thr Leu Val Leu Ser Ser Ala Ala Pro Ile Ser Ala Ala Phe
            20                  25                  30

Ala Glu Thr Pro Thr Lys Pro Lys Ala Ala Gln Thr Glu Lys Lys Thr
            35                  40                  45

Glu Lys Lys Pro Glu Asn Ser Asn Ser Glu Ala Ala Lys Lys Ala Leu
        50                  55                  60

Asn Asp Tyr Ile Trp Gly Leu Gln Tyr Asp Lys Leu Asn Ile Leu Thr
65                  70                  75                  80

His Gln Gly Glu Lys Leu Lys Asn His Ser Ser Arg Glu Ala Phe His
            85                  90                  95

Arg Pro Gly Glu Tyr Val Val Ile Glu Lys Lys Lys Gln Ser Ile Ser
            100                 105                 110

Asn Ala Thr Ser Lys Leu Ser Val Ser Ser Ala Asn Asp Asp Arg Ile
```

```
            115                 120                 125
Phe Pro Gly Ala Leu Leu Lys Ala Asp Gln Ser Leu Leu Glu Asn Leu
130                 135                 140

Pro Thr Leu Ile Pro Val Asn Arg Gly Lys Thr Thr Ile Ser Val Asn
145                 150                 155                 160

Leu Pro Gly Leu Lys Asn Gly Glu Ser Asn Leu Thr Val Glu Asn Pro
                    165                 170                 175

Ser Asn Ser Thr Val Arg Thr Ala Val Asn Asn Leu Val Glu Lys Trp
                180                 185                 190

Ile Gln Asn Tyr Ser Lys Thr His Ala Val Pro Ala Arg Met Gln Tyr
            195                 200                 205

Glu Ser Ile Ser Ala Gln Ser Met Ser Gln Leu Gln Ala Lys Phe Gly
        210                 215                 220

Ala Asp Phe Ser Lys Val Gly Ala Pro Leu Asn Val Asp Phe Ser Ser
225                 230                 235                 240

Val His Lys Gly Glu Lys Gln Val Phe Ile Ala Asn Phe Arg Gln Val
                    245                 250                 255

Tyr Tyr Thr Ala Ser Val Asp Ser Pro Asn Ser Pro Ser Ala Leu Phe
                260                 265                 270

Gly Ser Gly Ile Thr Pro Thr Asp Leu Ile Asn Arg Gly Val Asn Ser
            275                 280                 285

Lys Thr Pro Pro Val Tyr Val Ser Asn Val Ser Tyr Gly Arg Ala Met
290                 295                 300

Tyr Val Lys Phe Glu Thr Thr Ser Lys Ser Thr Lys Val Gln Ala Ala
305                 310                 315                 320

Ile Asp Ala Val Val Lys Gly Ala Lys Leu Lys Ala Gly Thr Glu Tyr
                    325                 330                 335

Glu Asn Ile Leu Lys Asn Thr Lys Ile Thr Ala Val Val Leu Gly Gly
                340                 345                 350

Asn Pro Gly Glu Ala Ser Lys Val Ile Thr Gly Asn Ile Asp Thr Leu
            355                 360                 365

Lys Asp Leu Ile Gln Lys Gly Ser Asn Phe Ser Ala Gln Ser Pro Ala
370                 375                 380

Val Pro Ile Ser Tyr Thr Thr Ser Phe Val Lys Asp Asn Ser Ile Ala
385                 390                 395                 400

Thr Ile Gln Asn Asn Thr Asp Tyr Ile Glu Thr Lys Val Thr Ser Tyr
                    405                 410                 415

Lys Asp Gly Ala Leu Thr Leu Asn His Asp Gly Ala Phe Val Ala Arg
                420                 425                 430

Phe Tyr Val Tyr Trp Glu Glu Leu Gly His Asp Ala Asp Gly Tyr Glu
            435                 440                 445

Thr Ile Arg Ser Arg Ser Trp Ser Gly Asn Gly Tyr Asn Arg Gly Ala
        450                 455                 460

His Tyr Ser Thr Thr Leu Arg Phe Lys Gly Asn Val Arg Asn Ile Arg
465                 470                 475                 480

Val Lys Val Leu Gly Ala Thr Gly Leu Ala Trp Glu Pro Trp Arg Leu
                    485                 490                 495

Ile Tyr Ser Lys Asn Asp Leu Pro Leu Val Pro Gln Arg Asn Ile Ser
                500                 505                 510

Thr Trp Gly Thr Thr Leu His Pro Gln Phe Glu Asp Lys Val Val Lys
            515                 520                 525

Asp Asn Thr Asp
        530
```

<210> SEQ ID NO 28
<211> LENGTH: 501
<212> TYPE: PRT
<213> ORGANISM: Bacillus alvei

<400> SEQUENCE: 28

```
Met Lys Lys Lys Ser Asn His Leu Lys Gly Arg Lys Val Leu Val Ser
 1               5                  10                  15

Leu Leu Val Ser Leu Gln Val Phe Ala Phe Ala Ser Ile Ser Ser Ala
            20                  25                  30

Ala Pro Thr Glu Pro Asn Asp Ile Asp Met Gly Ile Ala Gly Leu Asn
        35                  40                  45

Tyr Asn Arg Asn Glu Val Leu Ala Ile Gln Gly Asp Gln Ile Ser Ser
    50                  55                  60

Phe Val Pro Lys Glu Gly Ile Gln Ser Asn Gly Lys Phe Ile Val Val
65                  70                  75                  80

Glu Arg Asp Lys Lys Ser Leu Thr Thr Ser Pro Val Asp Ile Ser Ile
                85                  90                  95

Val Asp Ser Ile Thr Asn Arg Thr Tyr Pro Gly Ala Ile Gln Leu Ala
            100                 105                 110

Asn Lys Asp Phe Ala Asp Asn Gln Pro Ser Leu Val Met Ala Ala Arg
        115                 120                 125

Lys Pro Leu Asp Ile Ser Ile Asp Leu Pro Gly Leu Lys Asn Glu Asn
    130                 135                 140

Thr Ile Ser Val Gln Asn Pro Asn Tyr Gly Thr Val Ser Ser Ala Ile
145                 150                 155                 160

Asp Gln Leu Val Ser Thr Trp Gly Glu Lys Tyr Ser Ser Thr His Thr
                165                 170                 175

Leu Pro Ala Arg Leu Gln Tyr Ala Glu Ser Met Val Tyr Ser Gln Asn
            180                 185                 190

Gln Ile Ser Ser Ala Leu Asn Val Asn Ala Lys Val Leu Asn Gly Thr
        195                 200                 205

Leu Gly Ile Asp Phe Asn Ala Val Ala Asn Gly Glu Lys Lys Val Met
    210                 215                 220

Val Ala Ala Tyr Lys Gln Ile Phe Tyr Thr Val Ser Ala Gly Leu Pro
225                 230                 235                 240

Asn Asn Pro Ser Asp Leu Phe Asp Asp Ser Val Thr Phe Ala Glu Leu
                245                 250                 255

Ala Arg Lys Gly Val Ser Asn Glu Ala Pro Pro Leu Met Val Ser Asn
            260                 265                 270

Val Ala Tyr Gly Arg Thr Ile Tyr Val Lys Leu Glu Thr Thr Ser Lys
        275                 280                 285

Ser Asn Asp Val Gln Thr Ala Phe Lys Leu Leu Leu Asn Asn Pro Ser
    290                 295                 300

Glx Gln Ala Ser Gly Gln Tyr Lys Asp Ile Tyr Glu Asn Ser Ser Phe
305                 310                 315                 320

Thr Ala Val Val Leu Gly Gly Asp Ala Gln Thr His Asn Gln Val Val
                325                 330                 335

Thr Lys Asp Phe Asn Val Ile Gln Ser Val Ile Lys Asp Asn Ala Gln
            340                 345                 350

Phe Ser Ser Lys Asn Pro Ala Tyr Pro Ile Ser Tyr Thr Ser Val Phe
        355                 360                 365

Leu Lys Asp Asn Ser Ile Ala Ala Val His Asn Asn Thr Glu Tyr Ile
```

```
            370                 375                 380
Glu Thr Lys Thr Thr Glu Tyr Ser Lys Gly Lys Ile Lys Leu Asp His
385                 390                 395                 400

Ser Gly Ala Tyr Val Ala Gln Phe Glu Val Tyr Trp Asp Glu Phe Ser
            405                 410                 415

Tyr Asp Ala Asp Gly Gln Glu Ile Val Thr Arg Lys Ser Trp Asp Gly
            420                 425                 430

Asn Trp Arg Asp Arg Ser Ala His Phe Ser Thr Glu Ile Pro Leu Pro
            435                 440                 445

Pro Asn Ala Lys Asn Ile Arg Ile Phe Ala Arg Glu Cys Thr Gly Leu
            450                 455                 460

Ala Trp Glu Trp Trp Arg Thr Val Val Asp Glu Tyr Asn Val Pro Leu
465                 470                 475                 480

Ala Ser Asp Ile Asn Val Ser Ile Trp Gly Thr Thr Leu Tyr Pro Lys
            485                 490                 495

Ser Ser Ile Thr His
            500
```

<210> SEQ ID NO 29
<211> LENGTH: 512
<212> TYPE: PRT
<213> ORGANISM: Bacillus anthracis
<220> FEATURE:
<221> NAME/KEY: VARIANT
<222> LOCATION: 438, 440
<223> OTHER INFORMATION: Xaa = any amino acid

<400> SEQUENCE: 29

```
Met Ile Phe Leu Asn Ile Lys Lys Asn Thr Lys Arg Arg Lys Phe Leu
1               5                   10                  15

Ala Cys Leu Leu Val Ser Leu Cys Thr Ile His Tyr Ser Ser Ile Ser
            20                  25                  30

Phe Ala Glu Thr Gln Ala Gly Asn Ala Thr Gly Ala Ile Lys Asn Ala
            35                  40                  45

Ser Asp Ile Asn Thr Gly Ile Ala Asn Leu Lys Tyr Asp Ser Arg Asp
50                  55                  60

Ile Leu Ala Val Asn Gly Asp Lys Val Glu Ser Phe Ile Pro Lys Glu
65                  70                  75                  80

Ser Ile Asn Ser Asn Gly Lys Phe Val Val Glu Arg Glu Lys Lys
            85                  90                  95

Ser Leu Thr Thr Ser Pro Val Asp Ile Leu Ile Ile Asp Ser Val Val
            100                 105                 110

Asn Arg Thr Tyr Pro Gly Ala Val Gln Leu Ala Asn Lys Ala Phe Ala
            115                 120                 125

Asp Asn Gln Pro Ser Leu Leu Val Ala Lys Arg Lys Pro Leu Asn Ile
            130                 135                 140

Ser Ile Asp Leu Pro Gly Met Arg Lys Glu Asn Thr Ile Thr Val Gln
145                 150                 155                 160

Asn Pro Thr Tyr Gly Asn Val Ala Gly Ala Val Asp Asp Leu Val Ser
            165                 170                 175

Thr Trp Asn Glu Lys Tyr Ser Thr His Thr Leu Pro Ala Arg Met
            180                 185                 190

Gln Tyr Thr Glu Ser Met Val Tyr Ser Lys Ser Gln Ile Ala Ser Ala
            195                 200                 205

Leu Asn Val Asn Ala Lys Tyr Leu Asp Asn Ser Leu Asn Ile Asp Phe
            210                 215                 220
```

```
Asn Ala Val Ala Asn Gly Glu Lys Lys Val Met Val Ala Ala Tyr Lys
225                 230                 235                 240

Gln Ile Phe Tyr Thr Val Ser Ala Glu Leu Pro Asn Asn Pro Ser Asp
                245                 250                 255

Leu Phe Asp Asn Ser Val Thr Phe Asp Glu Leu Thr Arg Lys Gly Val
            260                 265                 270

Ser Asn Ser Ala Pro Pro Val Met Val Ser Asn Val Ala Tyr Gly Arg
        275                 280                 285

Thr Val Tyr Val Lys Leu Glu Thr Thr Ser Lys Ser Lys Asp Val Gln
    290                 295                 300

Ala Ala Phe Lys Ala Leu Leu Lys Asn Asn Ser Val Glu Thr Ser Gly
305                 310                 315                 320

Gln Tyr Lys Asp Ile Phe Glu Glu Ser Thr Phe Thr Ala Val Val Leu
                325                 330                 335

Gly Gly Asp Ala Lys Glu His Asn Lys Val Val Thr Lys Asp Phe Asn
            340                 345                 350

Glu Ile Arg Asn Ile Ile Lys Asp Asn Ala Glu Leu Ser Phe Lys Asn
        355                 360                 365

Pro Ala Tyr Pro Ile Ser Tyr Thr Ser Thr Phe Leu Lys Asp Asn Ala
    370                 375                 380

Thr Ala Ala Val His Asn Asn Thr Asp Tyr Ile Glu Thr Thr Thr Thr
385                 390                 395                 400

Glu Tyr Ser Ser Ala Lys Met Thr Leu Asp His Tyr Gly Ala Tyr Val
                405                 410                 415

Ala Gln Phe Asp Val Ser Trp Asp Glu Phe Thr Phe Asp Gln Asn Gly
            420                 425                 430

Lys Glu Val Leu Thr Xaa Lys Xaa Trp Glu Gly Ser Gly Lys Asp Lys
        435                 440                 445

Thr Ala His Tyr Ser Thr Val Ile Pro Leu Pro Pro Asn Ser Lys Asn
    450                 455                 460

Ile Lys Ile Val Ala Arg Glu Cys Thr Gly Leu Ala Trp Glu Trp Trp
465                 470                 475                 480

Arg Thr Ile Ile Asn Glu Gln Asn Val Pro Leu Thr Asn Glu Ile Lys
                485                 490                 495

Val Ser Ile Gly Gly Thr Thr Leu Tyr Pro Thr Ala Thr Ile Ser His
            500                 505                 510

<210> SEQ ID NO 30
<211> LENGTH: 485
<212> TYPE: PRT
<213> ORGANISM: Bacillus cereus

<400> SEQUENCE: 30

Met Lys Asn Phe Lys Gly Arg Lys Phe Leu Thr Cys Val Leu Val Ser
 1               5                  10                  15

Leu Cys Thr Leu Asn Tyr Ser Ser Ile Ser Phe Ala Glu Thr Gln Ala
            20                  25                  30

Gly His Ala Asn Asp Ile Thr Lys Asn Ala Ser Ser Ile Asp Thr Gly
        35                  40                  45

Ile Gly Asn Leu Thr Tyr Asn Asn Gln Glu Val Leu Ala Val Asn Gly
    50                  55                  60

Asp Lys Val Glu Ser Phe Val Pro Lys Glu Ser Ile Asn Ser Asn Gly
65                  70                  75                  80

Lys Phe Val Val Val Asp Val Arg Lys Asn His Leu Gln Arg His Gln
```

```
            85                  90                  95
Ser Ile Phe Arg Leu Leu Asp Ser Val Ala Asn Arg Thr Tyr Pro Gly
            100                 105                 110

Ala Val Gln Leu Ala Asn Lys Ala Phe Ala Asp Asn Gln Pro Ser Leu
            115                 120                 125

Leu Val Ala Lys Arg Lys Pro Leu Asn Ile Ser Ile Asp Leu Pro Gly
            130                 135                 140

Met Arg Lys Glu Asn Thr Ile Thr Val Gln Asn Pro Thr Tyr Gly Asn
145                 150                 155                 160

Val Ala Gly Ala Val Asp Asp Leu Val Ser Thr Trp Asn Glu Lys Tyr
                165                 170                 175

Ser Ala Thr His Thr Leu Pro Ala Arg Met Gln Tyr Thr Glu Ser Met
            180                 185                 190

Val Tyr Ser Lys Ala Gln Ile Ala Ser Ala Leu Asn Val Asn Ala Lys
            195                 200                 205

Tyr Leu Asp Asn Ser Leu Asn Ile Asp Phe Asn Ala Val Ala Asn Gly
            210                 215                 220

Glu Lys Lys Val Met Val Ala Ala Tyr Lys Gln Ile Phe Tyr Thr Val
225                 230                 235                 240

Ser Ala Glu Leu Pro Asn Asn Pro Ser Asp Leu Phe Asp Asn Ser Val
                245                 250                 255

Thr Phe Gly Glu Leu Thr Arg Lys Gly Val Ser Asn Ser Ala Pro Pro
            260                 265                 270

Val Met Val Ser Asn Val Ala Tyr Gly Arg Thr Val Tyr Val Lys Leu
            275                 280                 285

Glu Thr Thr Ser Lys Ser Lys Asp Val Gln Ala Ala Phe Lys Ala Leu
            290                 295                 300

Leu Lys Asn Asn Ser Val Glu Thr Ser Gly Gln Tyr Lys Asp Ile Phe
305                 310                 315                 320

Glu Glu Ser Thr Phe Thr Ala Val Val Leu Gly Gly Asp Ala Lys Glu
                325                 330                 335

His Asn Lys Val Val Thr Lys Asp Phe Asn Glu Ile Arg Asn Ile Ile
            340                 345                 350

Lys Asp Asn Ala Glu Leu Ser Phe Lys Asn Pro Ala Tyr Pro Ile Ser
            355                 360                 365

Tyr Thr Ser Thr Phe Leu Lys Asp Asn Ala Thr Ala Ala Val His Asn
            370                 375                 380

Asn Thr Asp Tyr Ile Glu Thr Thr Thr Glu Tyr Ser Ser Ala Lys
385                 390                 395                 400

Met Thr Leu Asp His Tyr Gly Ala Tyr Val Ala Gln Phe Asp Val Ser
                405                 410                 415

Trp Asp Gly Phe Thr Phe Asp Gln Asn Gly Lys Glu Ile Leu Thr His
            420                 425                 430

Lys Thr Trp Glu Gly Ser Gly Lys Asp Lys Thr Ala His Tyr Ser Thr
            435                 440                 445

Val Ile Pro Leu Pro Pro Asn Ser Lys Asn Ile Lys Ile Val Ala Arg
            450                 455                 460

Glu Cys Thr Gly Leu Ala Trp Glu Trp Trp Arg Thr Ile Ile Lys Met
465                 470                 475                 480

Asn Lys Met Phe His
                485

<210> SEQ ID NO 31
```

-continued

<211> LENGTH: 528
<212> TYPE: PRT
<213> ORGANISM: Listeria ivanovii

<400> SEQUENCE: 31

```
Met Lys Lys Ile Met Leu Leu Leu Met Thr Leu Leu Leu Val Ser Leu
 1               5                  10                  15

Pro Leu Ala Gln Glu Ala Gln Ala Asp Ala Ser Val Tyr Ser Tyr Gln
            20                  25                  30

Gly Ile Ile Ser His Met Ala Pro Pro Ala Ser Pro Pro Ala Lys Pro
        35                  40                  45

Lys Thr Pro Val Glu Lys Lys Asn Ala Ala Gln Ile Asp Gln Tyr Ile
    50                  55                  60

Gln Gly Leu Asp Tyr Asp Lys Asn Asn Ile Leu Val Tyr Asp Gly Glu
65                  70                  75                  80

Ala Val Lys Asn Val Pro Pro Lys Ala Gly Tyr Lys Glu Gly Asn Gln
                85                  90                  95

Tyr Ile Val Val Glu Lys Lys Lys Lys Ser Ile Asn Gln Asn Asn Ala
            100                 105                 110

Asp Ile Gln Val Ile Asn Ser Leu Ala Ser Leu Thr Tyr Pro Gly Ala
        115                 120                 125

Leu Val Lys Ala Asn Ser Glu Leu Val Glu Asn Gln Pro Asp Val Leu
    130                 135                 140

Pro Val Lys Arg Asp Ser Val Thr Leu Ser Ile Asp Leu Pro Gly Met
145                 150                 155                 160

Val Asn His Asp Asn Glu Ile Val Val Gln Asn Ala Thr Lys Ser Asn
                165                 170                 175

Ile Asn Asp Gly Val Asn Thr Leu Val Asp Arg Trp Asn Asn Lys Tyr
            180                 185                 190

Ser Glu Glu Tyr Pro Asn Ile Ser Ala Lys Ile Asp Tyr Asp Gln Glu
        195                 200                 205

Met Ala Tyr Ser Glu Ser Gln Leu Val Ala Lys Phe Gly Ala Ala Phe
    210                 215                 220

Lys Ala Val Asn Asn Ser Leu Asn Val Asn Phe Gly Ala Ile Ser Glu
225                 230                 235                 240

Gly Lys Val Gln Glu Glu Val Ile Asn Phe Lys Gln Ile Tyr Tyr Thr
                245                 250                 255

Val Asn Val Asn Glu Pro Thr Ser Pro Ser Arg Phe Phe Gly Lys Ser
            260                 265                 270

Val Thr Lys Glu Asn Leu Gln Ala Leu Gly Val Asn Ala Glu Asn Pro
        275                 280                 285

Pro Ala Tyr Ile Ser Ser Val Ala Tyr Gly Arg Asp Ile Phe Val Lys
    290                 295                 300

Leu Ser Thr Ser Ser His Ser Thr Arg Val Lys Ala Ala Phe Asp Ala
305                 310                 315                 320

Ala Phe Lys Gly Lys Ser Val Lys Gly Asp Thr Glu Leu Glu Asn Ile
                325                 330                 335

Ile Gln Asn Ala Ser Phe Lys Ala Val Ile Tyr Gly Gly Ser Ala Lys
            340                 345                 350

Asp Glu Val Glu Ile Ile Asp Gly Asp Leu Ser Lys Leu Arg Asp Ile
        355                 360                 365

Leu Lys Gln Gly Ala Asn Phe Asp Lys Lys Asn Pro Gly Val Pro Ile
    370                 375                 380

Ala Tyr Thr Thr Asn Phe Leu Lys Asp Asn Gln Leu Ala Val Val Lys
```

```
385                 390                 395                 400
Asn Asn Ser Glu Tyr Ile Glu Thr Thr Ser Lys Ala Tyr Ser Asp Gly
            405                 410                 415

Lys Ile Asn Leu Asp His Ser Gly Ala Tyr Val Ala Arg Phe Asn Val
            420                 425                 430

Thr Trp Asp Glu Val Ser Tyr Asp Ala Asn Gly Asn Glu Val Val Glu
            435                 440                 445

His Lys Lys Trp Ser Glu Asn Asp Lys Asp Lys Leu Ala His Phe Thr
            450                 455                 460

Thr Ser Ile Tyr Leu Pro Gly Asn Ala Arg Asn Ile Asn Ile His Ala
465                 470                 475                 480

Lys Glu Cys Thr Gly Leu Ala Trp Glu Trp Arg Thr Val Val Asp
            485                 490                 495

Asp Arg Asn Leu Pro Leu Val Lys Asn Arg Asn Val Cys Ile Trp Gly
            500                 505                 510

Thr Thr Leu Tyr Pro Ala Tyr Ser Asp Thr Val Asp Asn Pro Ile Lys
            515                 520                 525

<210> SEQ ID NO 32
<211> LENGTH: 534
<212> TYPE: PRT
<213> ORGANISM: Arcanobacterium pyogenes

<400> SEQUENCE: 32

Met Lys Arg Lys Ala Phe Ala Ser Leu Val Ala Ser Val Val Ala Ala
1               5                   10                  15

Ala Thr Val Thr Met Pro Thr Ala Ser Phe Ala Ala Gly Leu Gly Asn
            20                  25                  30

Ser Ser Gly Leu Thr Asp Gly Leu Ser Ala Pro Arg Val Ser Ile Ser
            35                  40                  45

Pro Met Asp Lys Val Asp Leu Lys Ser Ala Gln Glu Thr Asp Glu Thr
            50                  55                  60

Ser Val Asp Lys Tyr Ile Arg Gly Leu Glu Tyr Asp Pro Ser Gly Val
65              70                  75                  80

Leu Ala Val Lys Gly Glu Ser Ile Glu Asn Val Pro Val Thr Lys Asp
            85                  90                  95

Gln Leu Lys Asp Gly Thr Tyr Thr Val Phe Lys His Glu Arg Lys Ser
            100                 105                 110

Phe Asn Asn Leu Arg Ser Asp Ile Ser Ala Phe Asp Ala Asn Asn Ala
            115                 120                 125

His Val Tyr Pro Gly Ala Leu Val Leu Ala Asn Lys Asp Leu Ala Lys
            130                 135                 140

Gly Ser Pro Thr Ser Ile Gly Ile Ala Arg Ala Pro Gln Thr Val Ser
145                 150                 155                 160

Val Asp Leu Pro Gly Leu Val Asp Gly Lys Ser Lys Val Val Ile Asn
            165                 170                 175

Asn Pro Thr Lys Ser Ser Val Thr Gln Gly Met Asn Gly Leu Leu Asp
            180                 185                 190

Gly Trp Ile Gln Arg Asn Ser Lys Tyr Pro Asp His Ala Ala Lys Ile
            195                 200                 205

Phe Tyr Asp Glu Thr Met Val Thr Ser Lys Arg Gln Leu Glu Ala Lys
            210                 215                 220

Phe Gly Leu Gly Phe Glu Lys Val Ser Ala Lys Leu Asn Val Asp Phe
225                 230                 235                 240
```

Asp Ala Ile His Lys Arg Glu Arg Gln Val Ala Ile Ala Ser Phe Lys
             245                 250                 255

Gln Ile Tyr Tyr Thr Ala Ser Val Asp Thr Pro Thr Ser Pro His Ser
        260                 265                 270

Val Phe Gly Pro Asn Val Thr Ala Gln Asp Leu Lys Asp Arg Gly Val
    275                 280                 285

Asn Asn Lys Asn Pro Leu Gly Tyr Ile Ser Ser Val Ser Tyr Gly Arg
290                 295                 300

Gln Ile Phe Val Lys Leu Glu Thr Thr Ser Thr Ser Asn Asp Val Gln
305                 310                 315                 320

Ala Ala Phe Ser Gly Leu Phe Lys Ala Lys Phe Gly Asn Leu Ser Thr
                325                 330                 335

Glu Phe Lys Ala Lys Tyr Ala Asp Ile Leu Asn Lys Thr Arg Ala Thr
            340                 345                 350

Val Tyr Ala Val Gly Gly Ser Ala Arg Gly Gly Val Glu Val Ala Thr
        355                 360                 365

Gly Asn Ile Asp Ala Leu Lys Lys Ile Ile Lys Glu Glu Ser Thr Tyr
    370                 375                 380

Ser Thr Lys Val Pro Ala Val Pro Val Ser Tyr Ser Val Asn Phe Leu
385                 390                 395                 400

Lys Asp Asn Gln Leu Ala Ala Val Arg Ser Ser Gly Asp Tyr Ile Glu
                405                 410                 415

Thr Thr Ala Thr Thr Tyr Lys Ser Gly Glu Ile Thr Phe Arg His Gly
            420                 425                 430

Gly Gly Tyr Val Ala Lys Phe Gly Leu Lys Trp Asp Glu Ile Ser Tyr
        435                 440                 445

Asp Pro Gln Gly Lys Glu Ile Arg Thr Pro Lys Thr Trp Ser Gly Asn
    450                 455                 460

Trp Val Gly Arg Thr Leu Gly Phe Arg Glu Thr Ile Gln Leu Pro Ala
465                 470                 475                 480

Asn Ala Arg Asn Ile His Val Glu Ala Gly Ala Thr Gly Leu Ala
                485                 490                 495

Trp Asp Pro Trp Trp Thr Val Ile Asn Lys Lys Asn Leu Pro Leu Val
            500                 505                 510

Pro His Arg Glu Ile Val Leu Lys Gly Thr Thr Leu Asn Pro Trp Val
        515                 520                 525

Glu Glu Asn Val Lys Ser
    530

<210> SEQ ID NO 33
<211> LENGTH: 530
<212> TYPE: PRT
<213> ORGANISM: Listeria seeligeri

<400> SEQUENCE: 33

Met Lys Ile Phe Gly Leu Val Ile Met Ser Leu Leu Phe Val Ser Leu
1               5                   10                  15

Pro Ile Thr Gln Gln Pro Glu Ala Arg Asp Val Pro Ala Tyr Asp Arg
            20                  25                  30

Ser Glu Val Thr Ile Ser Pro Ala Glu Thr Pro Glu Ser Pro Pro Ala
        35                  40                  45

Thr Pro Lys Thr Pro Val Glu Lys Lys His Ala Glu Glu Ile Asn Lys
    50                  55                  60

Tyr Ile Trp Gly Leu Asn Tyr Asp Lys Asn Ser Ile Leu Val Tyr Gln
65                  70                  75                  80

```
Gly Glu Ala Val Thr Asn Val Pro Pro Lys Lys Gly Tyr Lys Asp Gly
                85                  90                  95

Ser Glu Tyr Ile Val Val Glu Lys Lys Lys Gly Ile Asn Gln Asn
                100                 105                 110

Asn Ala Asp Ile Ser Val Ile Asn Ala Ile Ser Ser Leu Thr Tyr Pro
                115                 120                 125

Gly Ala Leu Val Lys Ala Asn Arg Glu Leu Val Glu Asn Gln Pro Asn
    130                 135                 140

Val Leu Pro Val Lys Arg Asp Ser Leu Thr Leu Ser Val Asp Leu Pro
145                 150                 155                 160

Gly Met Thr Lys Lys Asp Asn Lys Ile Phe Val Lys Asn Pro Thr Lys
                165                 170                 175

Ser Asn Val Asn Asn Ala Val Asn Thr Leu Val Glu Arg Trp Asn Asp
                180                 185                 190

Lys Tyr Ser Lys Ala Tyr Pro Asn Ile Asn Ala Lys Ile Asp Tyr Ser
    195                 200                 205

Asp Glu Met Ala Tyr Ser Glu Ser Gln Leu Ile Ala Lys Phe Gly Thr
    210                 215                 220

Ala Phe Lys Ala Val Asn Asn Ser Leu Asn Val Asn Phe Glu Ala Ile
225                 230                 235                 240

Ser Asp Gly Lys Val Gln Glu Glu Val Ile Ser Phe Lys Gln Ile Tyr
                245                 250                 255

Tyr Asn Ile Asn Val Asn Glu Pro Thr Ser Pro Ser Lys Phe Phe Gly
                260                 265                 270

Gly Ser Val Thr Lys Glu Gln Leu Asp Ala Leu Gly Val Asn Ala Glu
            275                 280                 285

Asn Pro Pro Ala Tyr Ile Ser Ser Val Ala Tyr Gly Arg Gln Val Tyr
    290                 295                 300

Val Lys Leu Ser Ser Ser Ser His Ser Asn Lys Val Lys Thr Ala Phe
305                 310                 315                 320

Glu Ala Ala Met Ser Gly Lys Ser Val Lys Gly Asp Val Glu Leu Thr
                325                 330                 335

Asn Ile Ile Lys Asn Ser Ser Phe Lys Ala Val Ile Tyr Gly Gly Ser
                340                 345                 350

Ala Lys Glu Glu Val Glu Ile Ile Asp Gly Asn Leu Gly Glu Leu Arg
            355                 360                 365

Asp Ile Leu Lys Lys Gly Ser Thr Tyr Asp Arg Glu Asn Pro Gly Val
    370                 375                 380

Pro Ile Ser Tyr Thr Thr Asn Phe Leu Lys Asp Asn Asp Leu Ala Val
385                 390                 395                 400

Val Lys Asn Asn Ser Glu Tyr Ile Glu Thr Thr Ser Lys Ser Tyr Thr
                405                 410                 415

Asp Gly Lys Ile Asn Ile Asp His Ser Gly Gly Tyr Val Ala Gln Phe
            420                 425                 430

Asn Ile Ser Trp Asp Glu Val Ser Tyr Asp Glu Asn Gly Asn Glu Ile
            435                 440                 445

Lys Val His Lys Lys Trp Gly Glu Asn Tyr Lys Ser Lys Leu Ala His
    450                 455                 460

Phe Thr Ser Ser Ile Tyr Leu Pro Gly Asn Ala Arg Asn Ile Asn Ile
465                 470                 475                 480

Tyr Ala Arg Glu Cys Thr Gly Leu Phe Trp Glu Trp Trp Arg Thr Val
                485                 490                 495
```

```
Ile Asp Asp Arg Asn Leu Pro Leu Val Lys Asn Arg Asn Val Ser Ile
                500                 505                 510

Trp Gly Thr Thr Leu Tyr Pro Arg His Ser Asn Val Asp Asn Pro
        515                 520                 525

Ile Gln
    530

<210> SEQ ID NO 34
<211> LENGTH: 574
<212> TYPE: PRT
<213> ORGANISM: Streptococcus pyogenes

<400> SEQUENCE: 34

Met Lys Asp Met Ser Asn Lys Thr Phe Lys Lys Tyr Ser Arg Val
1               5                   10                  15

Ala Gly Leu Leu Thr Ala Ala Leu Ile Ile Gly Asn Leu Val Thr Ala
                20                  25                  30

Asn Ala Glu Ser Asn Lys Gln Asn Thr Ala Ser Thr Glu Thr Thr Thr
                35                  40                  45

Thr Asn Glu Gln Pro Lys Pro Glu Ser Ser Glu Leu Thr Thr Glu Lys
    50                  55                  60

Ala Gly Gln Lys Thr Asp Asp Met Leu Asn Ser Asn Asp Met Ile Lys
65                  70                  75                  80

Leu Ala Pro Lys Glu Met Pro Leu Glu Ser Ala Glu Lys Glu Lys
                85                  90                  95

Lys Ser Glu Asp Lys Lys Lys Ser Glu Glu Asp His Thr Glu Glu Ile
                100                 105                 110

Asn Asp Lys Ile Tyr Ser Leu Asn Tyr Asn Glu Leu Glu Val Leu Ala
                115                 120                 125

Lys Asn Gly Glu Thr Ile Glu Asn Phe Val Pro Lys Glu Gly Val Lys
                130                 135                 140

Lys Ala Asp Lys Phe Ile Val Ile Glu Arg Lys Lys Lys Asn Ile Asn
145                 150                 155                 160

Thr Thr Pro Val Asp Ile Ser Ile Ile Asp Ser Val Thr Asp Arg Thr
                165                 170                 175

Tyr Pro Ala Ala Leu Gln Leu Ala Asn Lys Gly Phe Thr Glu Asn Lys
                180                 185                 190

Pro Asp Ala Val Val Thr Lys Arg Asn Pro Gln Lys Ile His Ile Asp
                195                 200                 205

Leu Pro Gly Met Gly Asp Lys Ala Thr Val Glu Val Asn Asp Pro Thr
                210                 215                 220

Tyr Ala Asn Val Ser Thr Ala Ile Asp Asn Leu Val Asn Gln Trp His
225                 230                 235                 240

Asp Asn Tyr Ser Gly Gly Asn Thr Leu Pro Ala Arg Thr Gln Tyr Thr
                245                 250                 255

Glu Ser Met Val Tyr Ser Lys Ser Gln Ile Glu Ala Ala Leu Asn Val
                260                 265                 270

Asn Ser Lys Ile Leu Asp Gly Thr Leu Gly Ile Asp Phe Lys Ser Ile
                275                 280                 285

Ser Lys Gly Glu Lys Lys Val Met Ile Ala Ala Tyr Lys Gln Ile Phe
                290                 295                 300

Tyr Thr Val Ser Ala Asn Leu Pro Asn Asn Pro Ala Asp Val Phe Asp
305                 310                 315                 320

Lys Ser Val Thr Phe Lys Glu Leu Gln Arg Lys Gly Val Ser Asn Glu
                325                 330                 335
```

Ala Pro Pro Leu Phe Val Ser Asn Val Ala Tyr Gly Arg Thr Val Phe
            340                 345                 350

Val Lys Leu Glu Thr Ser Ser Lys Ser Asn Asp Val Glu Ala Ala Phe
            355                 360                 365

Ser Ala Ala Leu Lys Gly Thr Asp Val Lys Thr Asn Gly Lys Tyr Ser
370                 375                 380

Asp Ile Leu Glu Asn Ser Ser Phe Thr Ala Val Val Leu Gly Gly Asp
385                 390                 395                 400

Ala Ala Glu His Asn Lys Val Val Thr Lys Asp Phe Asp Val Ile Arg
            405                 410                 415

Asn Val Ile Lys Asp Asn Ala Thr Phe Ser Arg Lys Asn Pro Ala Tyr
            420                 425                 430

Pro Ile Ser Tyr Thr Ser Val Phe Leu Lys Asn Asn Lys Ile Ala Gly
            435                 440                 445

Val Asn Asn Arg Thr Glu Tyr Val Glu Thr Thr Ser Thr Glu Tyr Thr
            450                 455                 460

Ser Gly Lys Ile Asn Leu Ser His Arg Gly Ala Tyr Val Ala Gln Tyr
465                 470                 475                 480

Glu Ile Leu Trp Asp Glu Ile Asn Tyr Asp Asp Lys Gly Lys Glu Val
            485                 490                 495

Ile Thr Lys Arg Arg Trp Asp Asn Asn Trp Tyr Ser Lys Thr Ser Pro
            500                 505                 510

Phe Ser Thr Val Ile Pro Leu Gly Ala Asn Ser Arg Asn Ile Arg Ile
            515                 520                 525

Met Ala Arg Glu Cys Thr Gly Leu Ala Trp Glu Trp Trp Arg Lys Val
            530                 535                 540

Ile Asp Glu Arg Asp Val Lys Leu Ser Lys Glu Ile Asn Val Asn Ile
545                 550                 555                 560

Ser Gly Ser Thr Leu Ser Pro Tyr Gly Ser Ile Thr Tyr Lys
            565                 570

<210> SEQ ID NO 35
<211> LENGTH: 497
<212> TYPE: PRT
<213> ORGANISM: Streptococcus suis

<400> SEQUENCE: 35

Met Arg Lys Ser Ser His Leu Ile Leu Ser Ile Val Ser Leu Ala
1               5                   10                  15

Leu Val Gly Val Thr Pro Leu Ser Val Leu Ala Asp Ser Lys Gln Asp
            20                  25                  30

Ile Asn Gln Tyr Phe Gln Ser Leu Thr Tyr Glu Pro Gln Glu Ile Leu
            35                  40                  45

Thr Asn Glu Gly Glu Tyr Ile Asp Asn Pro Ala Thr Thr Gly Met
50                  55                  60

Leu Glu Asn Gly Arg Phe Val Val Leu Arg Arg Glu Lys Lys Asn Ile
65                  70                  75                  80

Thr Asn Asn Ser Ala Asp Ile Ala Val Ile Asp Ala Lys Ala Ala Asn
            85                  90                  95

Ile Tyr Pro Gly Ala Leu Leu Arg Ala Asp Gln Asn Leu Leu Asp Asn
            100                 105                 110

Asn Pro Thr Leu Ile Ser Ile Ala Arg Gly Asp Leu Thr Leu Ser Leu
            115                 120                 125

Asn Leu Pro Gly Leu Ala Asn Gly Asp Ser His Thr Val Val Asn Ser

```
            130                 135                 140
Pro Thr Arg Ser Thr Val Arg Thr Gly Val Asn Asn Leu Leu Ser Lys
145                 150                 155                 160

Trp Asn Asn Thr Tyr Ala Gly Glu Tyr Gly Asn Thr Gln Ala Glu Leu
                165                 170                 175

Gln Tyr Asp Glu Thr Met Ala Tyr Ser Met Ser Gln Leu Lys Thr Lys
            180                 185                 190

Phe Gly Thr Ser Phe Glu Lys Ile Ala Val Pro Leu Asp Ile Asn Phe
        195                 200                 205

Asp Ala Val Asn Ser Gly Glu Lys Gln Val Gln Ile Ile Asn Phe Lys
    210                 215                 220

Gln Ile Tyr Tyr Thr Val Ser Val Asp Glu Pro Glu Ser Pro Ser Lys
225                 230                 235                 240

Leu Phe Ala Glu Gly Thr Thr Val Glu Asp Leu Gln Arg Asn Gly Ile
                245                 250                 255

Thr Asp Glu Val Pro Pro Val Tyr Val Ser Ser Val Ser Tyr Gly Arg
            260                 265                 270

Ser Met Phe Ile Lys Leu Glu Thr Ser Ser Arg Ser Thr Gln Val Gln
        275                 280                 285

Ala Ala Phe Lys Ala Ala Ile Lys Gly Val Asp Ile Ser Gly Asn Ala
    290                 295                 300

Glu Tyr Gln Asp Ile Leu Lys Asn Thr Ser Phe Ser Ala Tyr Ile Phe
305                 310                 315                 320

Gly Gly Asp Ala Gly Ser Ala Ala Thr Val Val Ser Gly Asn Ile Glu
                325                 330                 335

Thr Leu Lys Lys Ile Ile Glu Glu Gly Ala Arg Tyr Gly Lys Leu Asn
            340                 345                 350

Pro Gly Val Pro Ile Ser Tyr Ser Thr Asn Phe Val Lys Asp Asn Arg
        355                 360                 365

Pro Ala Gln Ile Leu Ser Asn Ser Glu Tyr Ile Glu Thr Thr Ser Thr
    370                 375                 380

Val His Asn Ser Ser Ala Leu Thr Leu Asp His Ser Gly Ala Tyr Val
385                 390                 395                 400

Ala Lys Tyr Asn Ile Thr Trp Glu Glu Val Ser Tyr Asn Glu Ala Gly
                405                 410                 415

Glu Glu Val Trp Glu Pro Lys Ala Trp Asp Lys Asn Gly Val Asn Leu
            420                 425                 430

Thr Ser His Trp Ser Glu Thr Ile Gln Ile Pro Gly Asn Ala Arg Asn
        435                 440                 445

Leu His Val Asn Ile Gln Glu Cys Thr Gly Leu Ala Trp Glu Trp Trp
    450                 455                 460

Arg Thr Val Tyr Asp Lys Asp Leu Pro Leu Val Gly Gln Arg Lys Ile
465                 470                 475                 480

Thr Ile Trp Gly Thr Thr Leu Tyr Pro Gln Tyr Ala Asp Glu Val Ile
                485                 490                 495

Glu

<210> SEQ ID NO 36
<211> LENGTH: 527
<212> TYPE: PRT
<213> ORGANISM: Clostridium tetani

<400> SEQUENCE: 36

Met Asn Lys Asn Val Leu Lys Phe Val Ser Arg Ser Leu Leu Ile Phe
```

```
  1               5                   10                  15
Ser Met Thr Gly Leu Ile Ser Asn Tyr Asn Ser Asn Val Leu Ala
             20                  25                  30

Lys Gly Asn Val Glu Glu His Ser Leu Ile Asn Asn Gly Gln Val Val
             35                  40                  45

Thr Ser Asn Thr Lys Cys Asn Leu Ala Lys Asp Asn Ser Ser Asp Ile
 50                  55                  60

Asp Lys Asn Ile Tyr Gly Leu Ser Tyr Asp Pro Arg Lys Ile Leu Ser
 65                  70                  75                  80

Tyr Asn Gly Glu Gln Val Glu Asn Phe Val Pro Ala Glu Gly Phe Glu
                 85                  90                  95

Asn Pro Asp Lys Phe Ile Val Val Lys Arg Glu Lys Lys Ser Ile Ser
                100                 105                 110

Asp Ser Thr Ala Asp Ile Ser Ile Ile Asp Ser Ile Asn Asp Arg Thr
                115                 120                 125

Tyr Pro Gly Ala Ile Gln Leu Ala Asn Arg Asn Leu Met Glu Asn Lys
                130                 135                 140

Pro Asp Ile Ile Ser Cys Glu Arg Lys Pro Ile Thr Ile Ser Val Asp
145                 150                 155                 160

Leu Pro Gly Met Ala Glu Asp Gly Lys Lys Val Val Asn Ser Pro Thr
                165                 170                 175

Tyr Ser Ser Val Asn Ser Ala Ile Asn Ser Ile Leu Asp Thr Trp Asn
                180                 185                 190

Ser Lys Tyr Ser Ser Lys Tyr Thr Ile Pro Thr Arg Met Ser Tyr Ser
                195                 200                 205

Asp Thr Met Val Tyr Ser Gln Ser Gln Leu Ser Ala Ala Val Gly Cys
                210                 215                 220

Asn Phe Lys Ala Leu Asn Lys Ala Leu Asn Ile Asp Phe Asp Ser Ile
225                 230                 235                 240

Phe Lys Gly Glu Lys Lys Val Met Leu Leu Ala Tyr Lys Gln Ile Phe
                245                 250                 255

Tyr Thr Val Ser Val Asp Pro Pro Asn Arg Pro Ser Asp Leu Phe Gly
                260                 265                 270

Asp Ser Val Thr Phe Asp Glu Leu Ala Leu Lys Gly Ile Asn Asn Asn
                275                 280                 285

Asn Pro Pro Ala Tyr Val Ser Asn Val Ala Tyr Gly Arg Thr Ile Tyr
                290                 295                 300

Val Lys Leu Glu Thr Thr Ser Lys Ser Ser His Val Lys Ala Ala Phe
305                 310                 315                 320

Lys Ala Leu Ile Asn Asn Gln Asp Ile Ser Ser Asn Ala Glu Tyr Lys
                325                 330                 335

Asp Ile Leu Asn Gln Ser Ser Phe Thr Ala Thr Val Leu Gly Gly Gly
                340                 345                 350

Ala Gln Glu His Asn Lys Ile Ile Thr Lys Asp Phe Asp Glu Ile Arg
                355                 360                 365

Asn Ile Ile Lys Asn Asn Ser Val Tyr Ser Pro Gln Asn Pro Gly Tyr
                370                 375                 380

Pro Ile Ser Tyr Thr Thr Thr Phe Leu Lys Asp Asn Ser Ile Ala Ser
385                 390                 395                 400

Val Asn Asn Lys Thr Glu Tyr Ile Glu Thr Thr Ala Thr Glu Tyr Thr
                405                 410                 415

Asn Gly Lys Ile Val Leu Asp His Ser Gly Ala Tyr Val Ala Gln Phe
                420                 425                 430
```

```
Gln Val Thr Trp Asp Glu Val Ser Tyr Asp Glu Lys Gly Asn Glu Ile
        435                 440                 445

Val Glu His Lys Ala Trp Glu Gly Asn Asn Arg Asp Arg Thr Ala His
    450                 455                 460

Phe Asn Thr Glu Ile Tyr Leu Lys Gly Asn Ala Arg Asn Ile Ser Val
465                 470                 475                 480

Lys Ile Arg Glu Cys Thr Gly Leu Ala Trp Glu Trp Trp Arg Thr Ile
                485                 490                 495

Val Asp Val Lys Asn Ile Pro Leu Ala Lys Glu Arg Thr Phe Tyr Ile
                500                 505                 510

Trp Gly Thr Thr Leu Tyr Pro Lys Thr Ser Ile Glu Thr Lys Met
            515                 520                 525

<210> SEQ ID NO 37
<211> LENGTH: 529
<212> TYPE: PRT
<213> ORGANISM: Listeria monocytogenes

<400> SEQUENCE: 37

Met Lys Lys Ile Met Leu Val Phe Ile Thr Leu Ile Leu Ile Ser Leu
1               5                   10                  15

Pro Ile Ala Gln Gln Thr Glu Ala Lys Asp Ala Ser Ala Phe His Lys
            20                  25                  30

Glu Asp Leu Ile Ser Ser Met Ala Pro Pro Thr Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
```

```
            275                 280                 285
Pro Pro Ala Tyr Ile Ser Ser Val Ala Tyr Gly Arg Gln Val Tyr Leu
    290                 295                 300
Lys Leu Ser Thr Asn Ser His Ser Thr Lys Val Lys Ala Ala Phe Asp
305                 310                 315                 320
Ala Ala Val Ser Gly Lys Ser Val Ser Gly Asp Val Glu Leu Thr Asn
                325                 330                 335
Ile Ile Lys Asn Ser Ser Phe Lys Ala Val Ile Tyr Gly Gly Ser Ala
            340                 345                 350
Lys Asp Glu Val Gln Ile Ile Asp Gly Asn Leu Gly Asp Leu Arg Asp
        355                 360                 365
Ile Leu Lys Lys Gly Ala Thr Phe Asn Arg Glu Thr Pro Gly Val Pro
    370                 375                 380
Ile Ala Tyr Thr Thr Asn Phe Leu Lys Asp Asn Glu Leu Ala Val Ile
385                 390                 395                 400
Lys Asn Asn Ser Glu Tyr Ile Glu Thr Thr Ser Lys Ala Tyr Thr Asp
                405                 410                 415
Gly Lys Ile Asn Ile Asp His Ser Gly Gly Tyr Val Ala Gln Phe Asn
            420                 425                 430
Ile Ser Trp Asp Glu Ile Asn Tyr Asp Pro Gly Gly Asn Glu Ile Val
        435                 440                 445
Gln His Lys Asn Trp Ser Glu Asn Asn Lys Ser Lys Leu Ala His Phe
    450                 455                 460
Thr Ser Ser Ile Tyr Leu Pro Gly Asn Ala Arg Asn Ile Asn Val Tyr
465                 470                 475                 480
Ala Lys Glu Cys Thr Gly Leu Ala Trp Glu Trp Trp Arg Thr Val Ile
                485                 490                 495
Asp Asp Arg Asn Leu Pro Leu Val Lys Asn Arg Asn Ile Ser Ile Trp
            500                 505                 510
Gly Thr Thr Leu Tyr Pro Lys Tyr Ser Asn Ser Val Asp Asn Pro Ile
        515                 520                 525
Glu

<210> SEQ ID NO 38
<211> LENGTH: 512
<212> TYPE: PRT
<213> ORGANISM: Bacillus thuringiensis

<400> SEQUENCE: 38

Met Ile Phe Leu Asn Ile Lys Lys Asn Gly Lys Arg Arg Lys Phe Leu
1               5                   10                  15
Thr Cys Val Leu Val Ser Leu Cys Thr Leu Asn Tyr Ser Ser Thr Ser
            20                  25                  30
Phe Ala Glu Thr Gln Ala Gly His Ala Thr Asp Ile Thr Lys Asn Ala
        35                  40                  45
Ser Ser Ile Asp Thr Gly Ile Gly Asn Leu Thr Tyr Asn Asn Gln Glu
    50                  55                  60
Val Leu Ala Val Asn Gly Asp Lys Val Glu Ser Phe Val Pro Lys Glu
65                  70                  75                  80
Ser Ile Asn Ser Asn Gly Lys Phe Val Val Glu Arg Glu Lys Lys
                85                  90                  95
Ser Leu Thr Thr Ser Pro Val Asp Ile Ser Ile Asp Ser Val Ala
            100                 105                 110
Asn Arg Thr Tyr Pro Gly Ala Val Gln Leu Ala Asn Lys Ala Phe Ala
```

115                 120                 125
Asp Asn Gln Pro Ser Leu Leu Val Ala Lys Arg Lys Pro Leu Asn Ile
    130                 135                 140

Ser Ile Asp Leu Pro Gly Met Arg Lys Glu Asn Thr Ile Thr Val Gln
145                 150                 155                 160

Asn Pro Thr Tyr Gly Asn Val Ala Gly Ala Val Asp Asp Leu Val Ser
                165                 170                 175

Thr Trp Asn Glu Lys Tyr Ser Glu Thr His Thr Leu Pro Ala Arg Met
            180                 185                 190

Gln Tyr Thr Glu Ser Met Val Tyr Ser Lys Ser Gln Ile Ala Ser Ala
        195                 200                 205

Leu Asn Val Asn Ala Lys Tyr Leu Asp Asn Ser Leu Asn Ile Asp Phe
    210                 215                 220

Asn Ala Val Ala Asn Gly Glu Lys Lys Val Met Val Ala Ala Tyr Lys
225                 230                 235                 240

Gln Ile Phe Tyr Thr Val Ser Ala Glu Leu Pro Asn Asn Pro Ser Asp
                245                 250                 255

Leu Phe Asp Asn Ser Val Thr Phe Asp Glu Leu Thr Arg Lys Gly Val
            260                 265                 270

Ser Asn Ser Ala Pro Pro Val Met Val Ser Asn Val Ala Tyr Gly Arg
        275                 280                 285

Thr Val Tyr Val Lys Leu Glu Thr Thr Ser Lys Ser Lys Asp Val Gln
    290                 295                 300

Ala Ala Phe Lys Ala Leu Leu Lys Asn Asn Ser Val Glu Thr Ser Gly
305                 310                 315                 320

Gln Tyr Lys Asp Ile Phe Glu Glu Ser Thr Phe Thr Ala Val Val Leu
                325                 330                 335

Gly Gly Asp Ala Lys Glu His Asn Lys Val Val Thr Lys Asp Phe Asn
            340                 345                 350

Glu Ile Arg Asn Ile Ile Lys Asp Asn Ala Glu Leu Ser Phe Lys Asn
        355                 360                 365

Pro Ala Tyr Pro Ile Ser Tyr Thr Ser Thr Phe Leu Lys Asp Asn Ala
    370                 375                 380

Thr Ala Ala Val His Asn Asn Thr Asp Tyr Ile Glu Thr Thr Thr Thr
385                 390                 395                 400

Glu Tyr Ser Ser Ala Lys Met Thr Leu Asp His Tyr Gly Ala Tyr Val
                405                 410                 415

Ala Gln Phe Asp Val Ser Trp Asp Glu Phe Thr Phe Asp Gln Asn Gly
            420                 425                 430

Lys Glu Val Leu Thr His Lys Thr Trp Glu Gly Ser Gly Lys Asp Lys
        435                 440                 445

Thr Ala His Tyr Ser Thr Val Ile Pro Leu Pro Pro Asn Ser Lys Asn
    450                 455                 460

Ile Lys Ile Val Ala Arg Glu Cys Thr Gly Leu Ala Trp Glu Trp Trp
465                 470                 475                 480

Arg Thr Ile Ile Asn Glu Gln Asn Val Pro Leu Thr Asn Glu Ile Lys
                485                 490                 495

Val Ser Ile Gly Gly Thr Thr Leu Tyr Pro Thr Ala Ser Ile Ser His
            500                 505                 510